US012653566B2

(12) United States Patent     (10) Patent No.:   US 12,653,566 B2

Nilsson     (45) Date of Patent:     Jun. 16, 2026

(54) SURGICAL INSTRUMENTS WITH COMPLIANT MECHANISM DESIGN

(71) Applicant: Innovative Delta Technology, LLC, Moreland Hills, OH (US)

(72) Inventor: Carl Michael Nilsson, Moreland Hills, OH (US)

(73) Assignee: Innovative Delta Technology, LLC, Moreland Hills, OH (US)

( * ) Notice: Subject to any disclaimer, the term of this patent is extended or adjusted under 35 U.S.C. 154(b) by 307 days.

(21) Appl. No.: 18/310,180

(22) Filed: May 1, 2023

(65) Prior Publication Data

US 2023/0346411 A1     Nov. 2, 2023

Related U.S. Application Data

(60) Provisional application No. 63/336,505, filed on Apr. 29, 2022.

(51) Int. Cl.
    A61B 17/29     (2006.01)
(52) U.S. Cl.
    CPC .. A61B 17/2909 (2013.01); *A61B 2017/2923* (2013.01)
(58) Field of Classification Search
    CPC ........ A61B 17/2909; A61B 2017/2923; A61B 2017/00526; A61B 17/2816; A61B 17/3201; A61B 2090/0813; A61B 17/2804; A61B 17/1606; A61B 17/1611; A61B 17/8863
    See application file for complete search history.

(56) References Cited

U.S. PATENT DOCUMENTS

| | | | |
|---|---|---|---|
| 3,302,648 A | 2/1967 | Nelson | |
| 3,367,337 A | 2/1968 | Javna et al. | |
| 3,392,727 A | 7/1968 | Hanlon | |
| 3,616,497 A | 11/1971 | Esposito, Jr. | |

(Continued)

FOREIGN PATENT DOCUMENTS

DE     102019005383 A1     2/2021

OTHER PUBLICATIONS

The International Search Report and The Written Opinion of the International Searching Authority, or the Declaration of corresponding PCT Application No. PCT/US2023/020507, dated Jul. 24, 2023, 12 pages.

*Primary Examiner* — Richard G Louis

(74) *Attorney, Agent, or Firm* — Tucker Ellis LLP; Michael G. Craig; Bennett E. Kuhar

(57)          ABSTRACT

Techniques and/or systems are disclosed for a device for use as a tool. The device has a main component formed as a monolithic body. The monolithic body is configured to be selectably transformed by a user between an operational configuration and a non-operational configuration to allow for cleaning and sterilization of the device. Transformation of the device from the non-operational configuration to the operational configuration includes engaging two or more portions of the monolithic body in contact together to form an operational tool that can be operably manipulated by the user. The operational tool has a distal tool end, a proximal user engagement end, and one or more hinge points. The transformation from the operational configuration to the non-operational configuration includes disengaging the engaged portions from each other.

19 Claims, 27 Drawing Sheets

(56)          References Cited

U.S. PATENT DOCUMENTS

| | | | | |
|---|---|---|---|---|
| 3,629,912 | A | * | 12/1971 | Klopp .................... G03D 13/10 |
| | | | | 24/535 |
| 3,777,760 | A | | 12/1973 | Essner |
| 3,921,640 | A | * | 11/1975 | Freeborn ............. A61B 17/062 |
| | | | | 606/147 |
| 4,839,947 | A | * | 6/1989 | Cohen .................... D06F 55/02 |
| | | | | 24/562 |
| 7,615,053 | B2 | | 11/2009 | McKinley |

* cited by examiner

SURGICAL INSTRUMENTS WITH COMPLIANT MECHANISM DESIGN

CROSS-REFERENCE TO RELATED APPLICATION

This application claims priority to U.S. provisional application No. 63/336,505, entitled IMPROVED SURGICAL INSTRUMENTS WITH COMPLIANT MECHANISM DESIGN, filed Apr. 29, 2022, which is incorporated herein by reference in its entirety.

BACKGROUND

Surgical instruments, such as various types of rongeurs, forceps and benders, are well known in the surgical community. These surgical instruments typically include multiple components that are connected with joints that use pins, screws or other means to allow for complex movement between the individual components. The design of conventional surgical implements, particularly those with multipart joints, inherently include tangential surfaces, cavities and thin, inner lumen that facilitate capillary action and draw biological fluid into those locations within the surgical instrument, making it difficult to properly clean and sterilize the surgical instrument completely. Biological fluid trapped in those locations is often not removed prior to sterilization resulting in a potential hazard of carcinogens remaining on the surgical instrument after the cleaning and sterilization process.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

In one implementation, there is provided a device for use as a tool. The device can comprise a main component formed as a monolithic body. The monolithic body is configured to be selectably transformed by a user between an operational configuration and a non-operational configuration. Transformation of the device from the non-operational configuration to the operational configuration can comprise engaging two or more portions of the monolithic body in contact together to form an operational tool that can be operably manipulated by the user. The operational tool can comprise a distal tool end, a proximal user engagement end, and one or more hinge points. The transformation from the operational configuration to the non-operational configuration can comprise disengaging the engaged portions from each other.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein:

FIG. 15A illustrates the CMD surgical instrument in the neutral position. FIG. 15B illustrates the CMD surgical instrument in the open position. FIG. 15C illustrates the CMD surgical instrument in the closed position.

FIG. 28A is a perspective view of one side of the CMD surgical instrument. FIG. 28B is a perspective view of an opposing side of the CMD surgical instrument.

DETAILED DESCRIPTION

Figure 1:
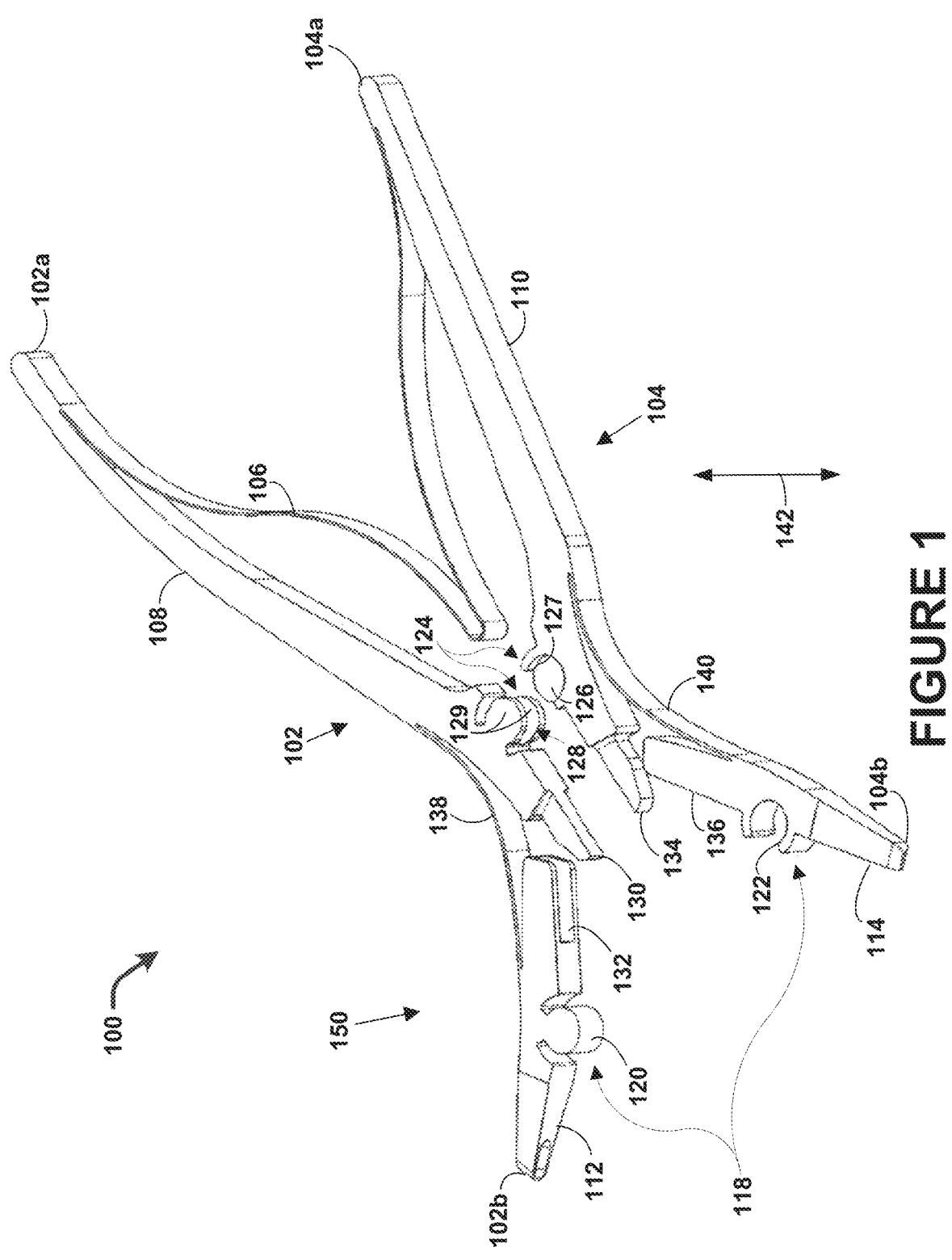
FIG. 1 is a component diagram illustrating an example implementation of a CMD surgical instrument in accordance with this disclosure in a cleaning position.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

The word "exemplary" is used herein to mean serving as an example, instance or illustration. Any aspect or design described herein as "exemplary" is not necessarily to be construed as advantageous over other aspects or designs.

Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

This disclosure is directed to surgical instruments having compliant mechanism designs, referred to herein as CMD surgical instruments. The CMD surgical instruments include a compliant mechanism that achieves force and motion transmission through elastic body deformation. In this manner, the CMD surgical instruments gain some or all of their motion from the relative flexibility of its members rather than from rigid-body joints alone.

The CMD surgical instruments of this disclosure are configured to perform their customary tasks, such as grasping or cutting bone and other tissue, and other functions, without relying solely on movable joints. Compared with conventional surgical instruments, the CMD surgical instruments of this disclosure are made of fewer components than contemporary designs, are simpler and less expensive to manufacture than existing instruments, and only have large cavities which do not allow for any capillary action to occur and hence all biological fluid can be completely removed during the cleaning process resulting in a completely clean, sterilized and carcinogen free surgical instrument. As an example, the CMD surgical instruments of this disclosure reduce the number (e.g., or do not include any) tangential surfaces or surfaces that form capillary cavities and cause blood and other fluids to be drawn into and collected within the cavities. Conventional surgical instruments are generally held together by inserting a screw or pin through a hole that is not sealed and draws in fluids. Biological remnants and particulate from the fluids drawn into these cavities can only be removed by removing the screw and disassembling the components.

The CMD surgical instruments disclosed herein allow for easier and more effective rinsing, cleaning, and sterilization of the surgical instruments. The cleaning and sterilization of surgical instruments are important considerations for medical providers, such as hospitals. For example, a frequent occurrence in modern surgical instruments is that "sterile dirt" is often left behind after cleaning and sterilization because rinsing will not remove all of the blood and other bodily fluids (e.g., and their contents) disposed between parallel surfaces of lumen cavities around screw threads and other cavities. In some instances, dried, biological remnants can be found between parallel surfaces of lumen cavities around screw threads after cleaning and sterilization. This is one reason some hospitals prefer disposable surgical instruments or desire a surgical instrument with improved cleaning and sterilization outcomes such as that provided by the CMD surgical instruments of this disclosure.

The CMD surgical instruments mitigate or eliminate the presence of tangential surfaces or capillary cavities thereby making the CMD surgical instruments easier to clean and sterilize. Other advantages of CMD surgical instruments include reducing the part count, simplifying the production process, and lowering the price/cost. For example, the CMD surgical instruments of this disclosure generally have a reduced number of parts by including resilient parts instead of springs, pins, and traditional rigid hinges. Thus, the number of components required for a surgical instrument with compliant mechanism can be considerably less than for a conventionally designed and manufactured version of the same mechanism. CMD surgical instruments can be easier to manufacture because they lend themselves well to various manufacturing processes including, but not limited to, machining, stamping, laser cutter, water-jet cutter, 3D printing, and electrical discharge machining (EDM). Because the CMD surgical instruments provide motion from resilient regions, many compliant mechanisms can be fabricated from planar sheets of material.

There are at least four different mechanical systems utilized by compliant mechanisms. One system comprises single hinge point instruments and tools, such as pliers, forceps, and scissors. This system includes instruments and tools having one rotational axis and two solid shafts. Another system comprises a dual hinge point mechanism. This system includes instruments and tools such as rongeurs and rod manipulators that have two rotational axes with the distance between the rotational axes, which significantly increases grasping strength. Both the single and dual hinge point instruments can either be "compressors" or "distractors". Closing the ties of a "compressor" causes a closing of the tip of the instrument (e.g., scissors, pliers, and forceps). Closing the ties of a "distractor" causes an opening of the tip of the instrument (e.g., spreaders). A third system can be found in Kerrisons, where actuating the resilient member, or trigger, on a pistol type grip causes a sliding motion of one long member with respect to the other. A forth system is a rolling joint, which can be utilized in a French Bender, which will be described later in more detail.

The compliant mechanisms of this disclosure are applicable any device for use as a tool, and not merely surgical instruments. The device can comprise a main component formed as a monolithic body. The monolithic body is configured to be selectably transformed by a user between an operational configuration and a non-operational configuration. The non-operational configuration can comprise a configuration in which the device is configured for cleaning and sterilization by the user. Transformation of the device from the non-operational configuration to the operational configuration can comprise engaging two or more portions of the monolithic body in contact together to form an operational tool that can be operably manipulated by the user. As an example, the device can comprise a monolithic body, or integrally formed body, comprising a first member and second member. The operational tool can comprise a distal tool end, a proximal user engagement end, and one or more hinge points. The transformation from the operational configuration to the non-operational configuration can comprise disengaging the engaged portions from each other.

Referring now the FIGURES, there are illustrated various implementations of devices having a compliant mechanism design. The devices generally do not contain tangential surface contacts and do not include cavities of a size that facilitate capillary action when the device is disposed in the non-operational configuration, or cleaning configuration.

Figure 2:
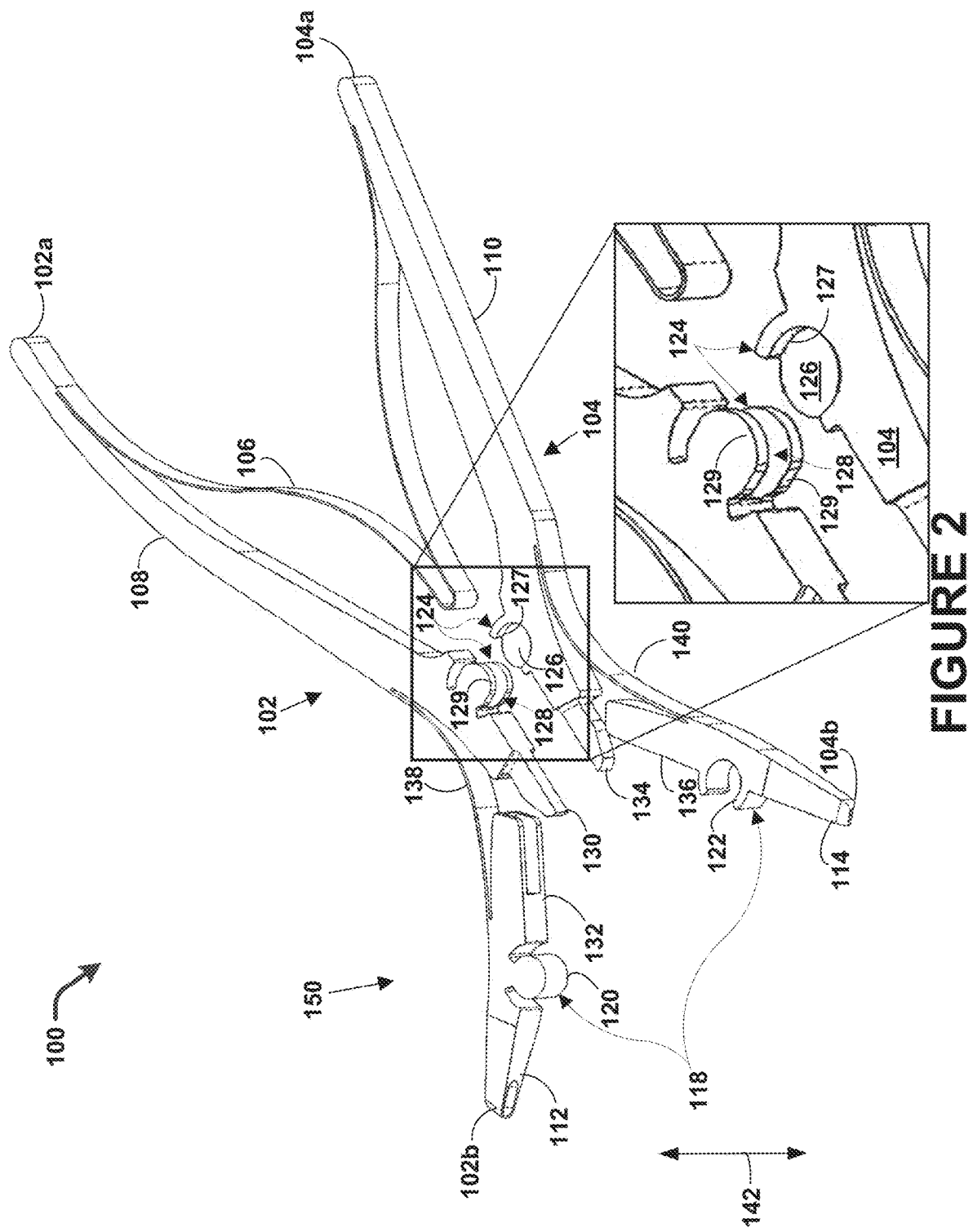
FIG. 2 is a component diagram illustrating a partial exploded view of the CMD surgical instrument of FIG. 1.
Figure 3:
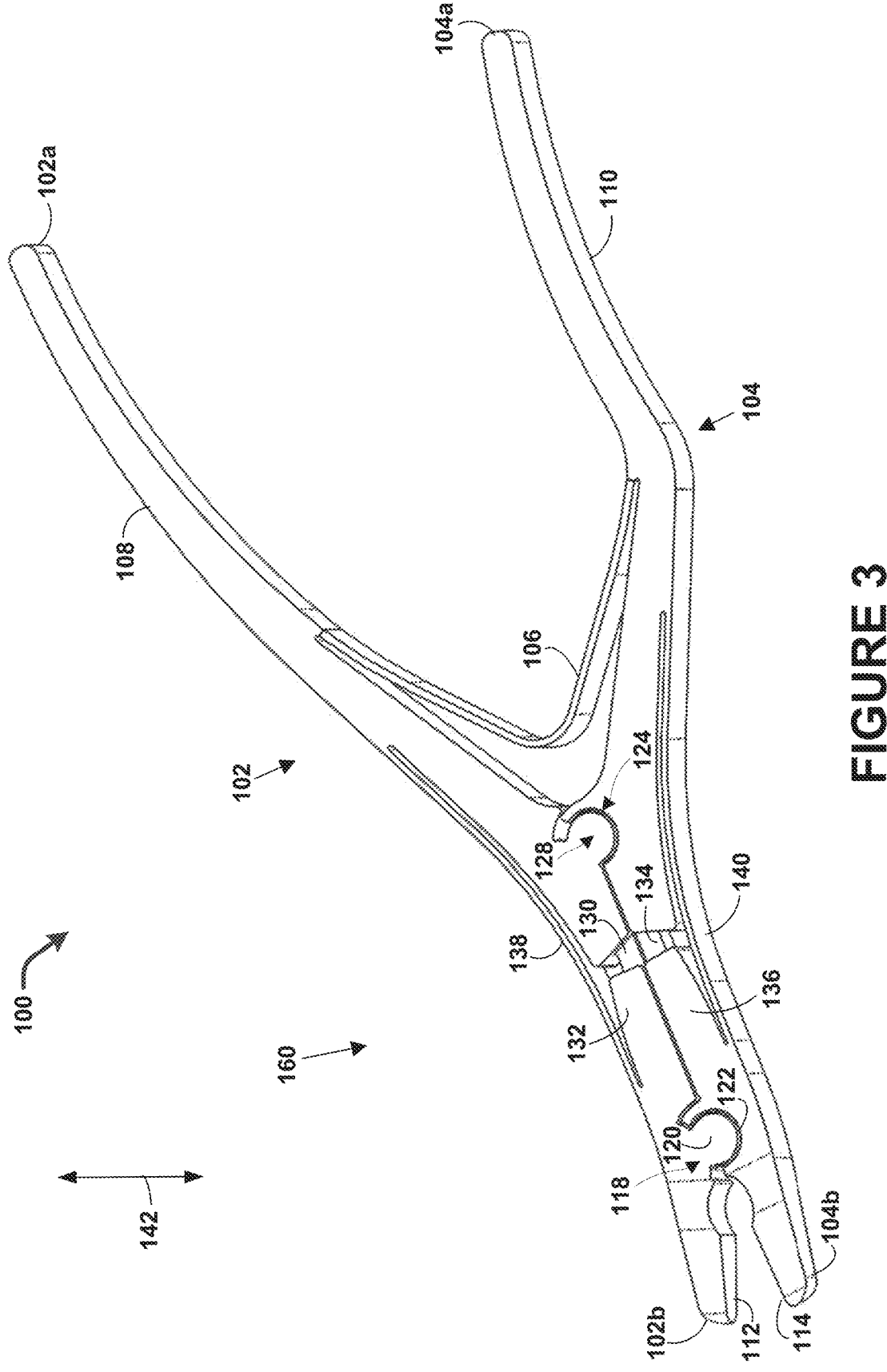
FIG. 3 is a component diagram illustrating the CMD surgical instrument of FIG. 1 in a surgical use position.
Figure 4:
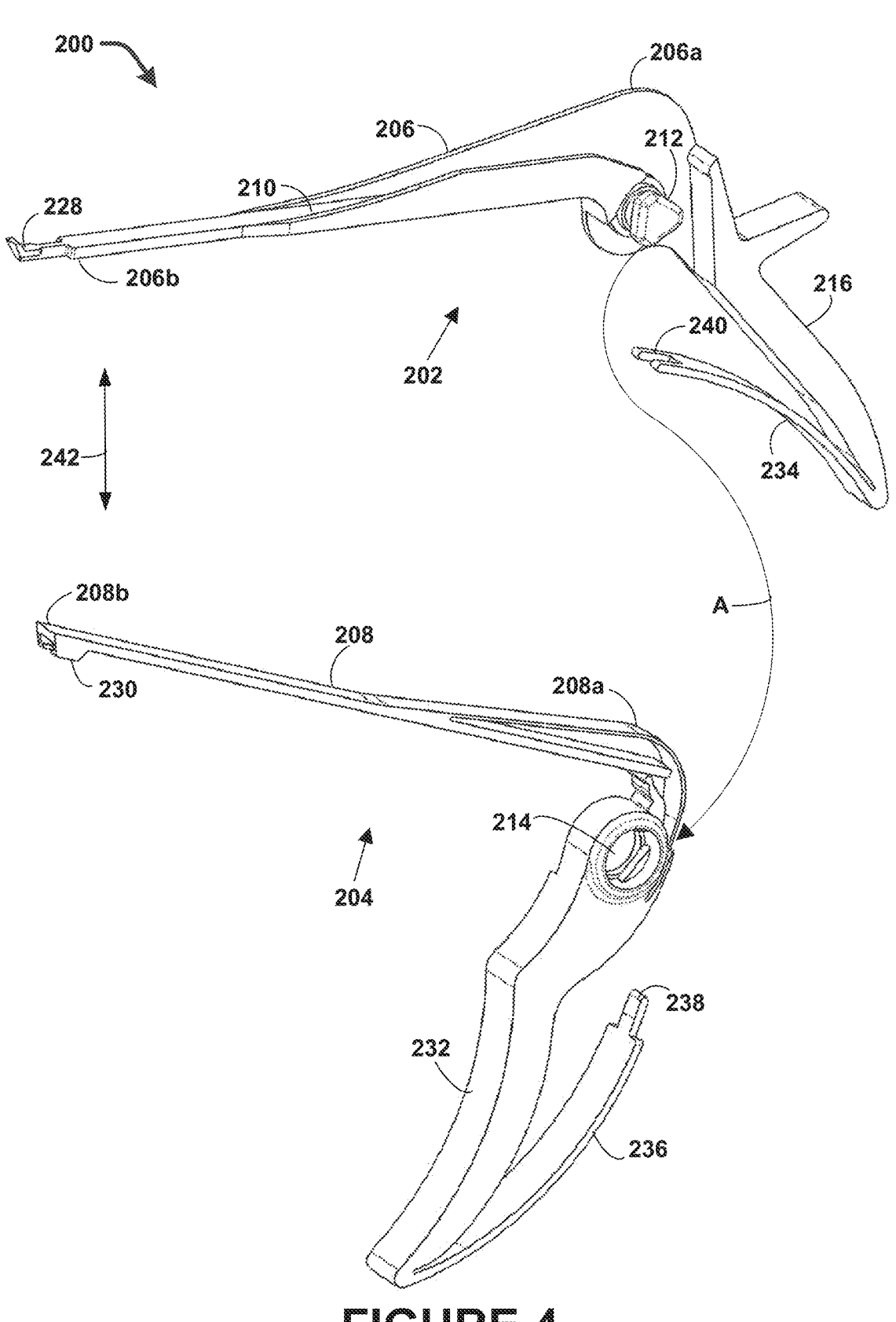
FIG. 4 is a component diagram illustrating another example implementation of a CMD surgical instrument in accordance with this disclosure.

Referring now to FIGS. 1 through 3, there is illustrated a first example implementation of a CMD device and, in particular, a CMD surgical instrument. In this implementation, the CMD surgical instrument comprises a CMD rongeur 100, which employs a dual hinge point. The CMD rongeur 100 can be formed from a single piece of metal material or elastomeric polymer. In some implementations, the CMD rongeur 100 is cut from a single piece of metal, such as a metal sheet.

The CMD rongeur 100 can comprise a first member 102, having a proximal end 102a and distal end 102b, and a second member 104, having a proximal end 104a and distal end 104b. A biasing member 106 extends between the first and second members 102, 104 and is integrally formed with the first and second members 102, 104 with one end (e.g., a first end) of the biasing member 106 connected to the first member 102 at or near the proximal end 102a and the other end (e.g., a second end) of the biasing member 106 connected to the second member 104 at or near the proximal end 104a. As an example, the biasing member 106 can have a first end and a second end and the biasing member 106 can extend between the first member 102 and the second member 104 with the first end connected to and integrally formed with the first member 102 and the second end connected to and integrally formed with the second member 104. In effect, the first member 102 and second member 104 are interconnected via the biasing member 106 which provides an integrally formed CMD rongeur 100, having a monolithic body, that can be fabricated from a single sheet of metal. Further, the biasing member 106 configured to apply a biasing force to the proximal ends 102a, 104a of the respective first and second members 102, 104.

Fabricating the CMD rongeur 100 from a single sheet of metal can result in generally flat portions or sections. As an example, the first and second members 102, 104 can be flat on the top and bottom. If it is desirable to use a different material for the biasing member 106 than for the first and second members 102, 104, then an alternative is to weld, pin or screw the biasing member 106 to the first and second members 102, 104, while maintaining large, non-tangential surfaces. The pins and screws of such an example implementation are not joints and hence would not create any capillary action.

FIGS. 1 and 2 show the CMD rongeur 100 after manufacturing, with the CMD rongeur 100 disposed in a non-operational configuration, or cleaning configuration, which allows for complete cleaning and sterilization of the surgical instrument. FIG. 3 shows the CMD rongeur 100 in an operational configuration which renders the CMD rongeur 100 functional to perform surgical procedures.

In this implementation, the first and second members 102, 104 each have a handle 108, 110 disposed at respective proximal ends 102a, 104a and each have a jaw 112, 114 disposed at respective distal ends 102b, 104b. The jaws 112, 114 oppose one another and are configured to cooperatively engage each other to exert a biting or grasping force. In some implementations, the jaws 112, 114 include an engaging component such as one or more teeth. The biasing member 106 is a flexible, resilient member that is configured to apply a biasing force to the proximal ends 102a, 104a of the respective first and second members 102, 104, such as to the handles 108, 110, when the first and second members are forced towards each other as described in more detail below. In some non-limiting examples, the biasing member 106 can be curved.

Disposed between the proximal and distal ends 102a, 102b, 104a, 104b of the first and second members 102, 104 are a hinge 118 and a second hinge 124. The hinge 118 is disposed proximate to the jaws 112, 114 and distal to the second hinge 124 of the CMD rongeur 100. As shown in FIGS. 1-2, the hinge 118 can comprise a first portion on the first member 102, such as a boss 120, that is configured to mate with a complementary second portion on the second member 104, such as a complementary socket 122 adapted to receive the boss 120, to form the hinge 118 or pivot. The mated first and second portions form a first hinge point and are configured to mechanically interact to render the hinge 118 pivotable. As an example, mating the boss 120 with the complementary socket 122 renders the hinge 118 functional or pivotable. In this particular implementation, the first member 102 comprises the boss 120 and the second member 104 comprises the socket 122. But, it should be understood from this disclosure that in other implementations the second member can comprise the boss and the first member can comprise the complementary socket of the hinge or pivot.

The second hinge 124 is disposed proximate to the handles 108, 110 and proximal to the hinge 118 of the CMD rongeur 100. As shown in FIGS. 1-2, the second hinge 124 can comprise a first portion on the first member 102, such as an engaging protrusion 126, that is configured to mate with a complementary second portion on the second member 104, such as a complementary slot 128 adapted to receive the engaging protrusion 126, to form the second hinge 124 or pivot. The mated first and second portions form a second hinge point and are configured to mechanically interact to render the second hinge 124 pivotable. As an example, mating the engaging protrusion 126 with the complementary slot 128 renders the second hinge 124 functional or pivotable. In this implementation, the second member 104 comprises the engaging protrusion 126 and the first member 102 comprises the slot 128. But, it should be understood from this disclosure that in other implementations the first member can comprise the engaging protrusion and the second member can comprise the complementary slot of the second hinge or pivot.

The distance between the pivot points defined by the hinge 118 and the second hinge 124 produce a corresponding bite force ratio. As the distance between the pivot points is varied, the bite force varies. As an example, the two hinges in this implementation can produce a bite ratio of 6:1.

In this implementation, the first member 102 can further comprise an intermediate protrusion 130 and a corresponding pocket 132 having an opening configured to receive the intermediate protrusion 130 therein. The intermediate protrusion 130 and corresponding pocket 132 of the first member 102 are disposed between the boss 120 of the hinge 118 and the slot 128 of the second hinge 124. The intermediate protrusion 130 is configured to engage the pocket 132 by slidably inserting the intermediate protrusion 130 into the opening in the pocket 132. Mirroring the first member 102, the second member 104 can comprise an intermediate protrusion 134 and a corresponding pocket 136 having an opening configured to receive the intermediate protrusion 134 therein. The intermediate protrusion 134 and corresponding pocket 136 of the second member 104 are positioned between the socket 122 of the hinge 118 and the engaging protrusion 126 of the second hinge 124. The intermediate protrusion 134 is configured to engage the pocket 136 by slidably inserting the intermediate protrusion 134 into the opening in the pocket 136.

In this implementation, the first and second members 102, 104 each comprise a resilient member 138, 140. The resilient member 138 of the first member 102 is a thin flexible band disposed lateral to the slot 128, intermediate protrusion 130, and pocket 132 approximately in the middle of the first member 102. The resilient member 140 of the second member 104 is a thin flexible band disposed lateral to the engaging protrusion 126, intermediate protrusion 134, and pocket 136 approximately in the middle of the second member 104.

The resilient members 138, 140 serve the purpose of stabilizing the CMD rongeur 100 by holding everything together in a manner analogous to ligaments of a biological joint. The mated pairs comprising the intermediate protrusion and associated pocket 130/132, 134/136 serve the purpose of transferring force generated (e.g., applied) by the motion of one joint, represented by the second hinge 124, to another joint, represented by the hinge 118. The mated pairs comprising the intermediate protrusion and associated pocket 130/132, 134/136 transfer this motion generated by movement of the joints by applying a bias in the medial direction when the CMD rongeur 100 is actuated, such as by forcing or manually squeezing the handles 108, 110 together.

FIGS. 1 through 3 illustrate that the CMD rongeur 100 can transition from the non-operational configuration 150 or cleaning configuration, as shown in FIGS. 1 and 2, to an operational configuration 160, as shown in FIG. 3, by performing the following sequence of steps. First, the boss 120 is configured to be mated with the complementary socket 122 by manually lifting, along vertical axis 142, the boss-containing part of the first member 102 out of planar alignment with the second member 104. The boss-containing part of the first member 102 is moved in the direction of the complementary socket 122 of the second member 104 until the boss 120 is aligned directly over or under the complementary socket 122. Finally, the boss 120 is moved linearly by lowering the boss 120 into the socket 122 to selectably insert the boss 120 into the complementary socket 122. This reestablishes the substantially coplanar alignment of the first member 102 and second member 104 and forms the hinge 118 or pivot.

Second, the engaging protrusion 126 is configured to be mated with the complementary slot 128 by slidably inserting the engaging protrusion 126 into the slot 128 such that the engaging protrusion 126 is sandwiched between two shelves 129 that define the slot 128. Each shelf 129 can have a circular shape with top and bottom surfaces that are parallel and flat. The distance or space between the two shelves 129 defines the height of the slot 128. Each shelf 129 has a height defined by the distance between the top and bottom surfaces of the shelf 129.

Thus, to summarize, the CMD rongeur 100 can transition from the non-operational configuration 150, or cleaning configuration, to the operational configuration 160 by performing the following sequence of steps. First, inserting the boss 120 into the complementary socket 122 to mate the boss 120 with the complementary socket 122. Mating the boss 120 with the complementary socket 122 forms the hinge. And, once mated, the first member 102 and the second member 104 are substantially coplanar. Second, mating the engaging protrusion 126 with the complementary slot 128 by slidably inserting the engaging protrusion 126 into the complementary slot 128 such that the engaging protrusion 126 is sandwiched between two shelves 129 defining the slot 128.

The engaging protrusion 126 has a circular shape with top and bottom surfaces that are parallel and flat. The engaging protrusion 126 has a height defined as the distance between its top and bottom surface. The height of the engaging protrusion 126 is less than the height of the slot 128 so that the engaging protrusion 126 can slide into, and be mated with, the slot 128 when the engaging protrusion 126 and slot 128 are appropriately oriented, or aligned, for insertion.

In this implementation, the top and bottom surfaces of the engaging protrusion 126 are recessed from the top and bottom surfaces of the second member 104 thereby forming a recess 127 above and below the engaging protrusion 126. The height of the engaging protrusion 126 is less than the height of the second member 104, which is defined as the distance between the top and bottom surfaces of the second member 104. The height of the recesses 127 is either the distance between the top surface of the engaging protrusion 126 and the top surface of the second member 104, or the bottom surface of the engaging protrusion 126 and the bottom surface of the second member 104. The height of the recesses 127 is equal to or slightly larger than the height of the shelves 129. In this manner, the surfaces of the shelves 129 are approximately flush with the surfaces of the second member 104 when the engaging protrusion 126 is inserted into the slot 128 and the shelves 129 are positioned in the recesses 127.

The two shelves that create the slot 128 can be circular with two parallel, flat surfaces 128a. The distance between those two parallel surfaces is smaller than the opening of the protrusion 126. This allows the protrusion 126 to slide into the slot 128 and the shelves 129 to slide into the recesses 127, which is done at a particular angle between the first and second members 102 and 104. During the assembly of the CMD rongeur 100, the biasing member 106 and the resilient members 138, 140 are stressed and want to return to a lower stress condition. This causes a rotation of the slot 128 with respect to the engaging protrusion 126 and hence the two components cannot separate from each other anymore, since the two parallel, flat surfaces are no longer aligned with the narrow opening. For example, the biasing member 106 is compressed during this assembly process and hence biases handles 108 and 110 away from each other. Assembling the first and second hinges 118, 124 causes each of the intermediate protrusions 130, 134 to be slidably inserted into their respective pockets 132, 136 and correspondingly engage with the walls of the pocket 132, 136. As another example, resilient members 138 and 140 initially have a concave shape prior to assembly. But the assembly process causes the resilient members 138 and 140 to assume a more convex shape. As the resilient members 138 and 140 try to return elastically to a concave shape they push the inner joint 130/132 and 134/136 closer together.

The practical operation of the CMD rongeur 100 begins with actuating the CMD rongeur 100 by forcing the first and second members 102, 104 towards each other, such as by manually squeezing the handles 108, 110 together. Forcing the handles 108, 110 towards each other causes pivoting at the second hinge 124. This pivoting at the second hinge 124 causes the intermediate protrusions 130, 134 to push outward against the pockets 132, 136. This outward action causes a rotation of the distal sections of the first and second members 102 and 104 due to the hinge 118. The movements are restricted by the resilient members 138 and 140, which act similar to ligaments to restore the original assembled position (e.g., the operational configuration). Due to the rotation of the distal sections of the first and second members 102 and 104, the opposing jaws 112 and 114 move towards each other to close in a biting fashion.

The CMD rongeur 100 can transition from the operational configuration 160, to the non-operational configuration 150, or cleaning configuration, by first disengaging the second hinge 124 followed by disengaging the hinge 118. The second hinge 124 can be disengaged by removing the engaging protrusion 126 from the slot 128 by linearly moving the engaging protrusion 126 and slot 128 in opposite directions away from each other while maintaining alignment of the two shelves 129 with the narrow portion of the two recesses 127. Next, the hinge 118 can be disengaged by removing the boss 120 from the socket 122 by linearly moving the boss 120 relative to the socket 122, such as vertically along axis 142, such that the first member 102 and the second member 104 are not in coplanar alignment. The boss-containing part of the first member 102 can then be moved in a direction away from the complementary socket 122 of the second member 104 after which the first member 102 and second member 104 can be placed into substantially coplanar alignment. Disengaging the first and second hinges 118, 124 causes the intermediate protrusions 130, 134 to disengage from their associated pockets 132, 136 respectively. This places the CMD rongeur 100 in the non-operational configuration 150. Disposing the CMD rongeur 100 in the non-operational configuration 150 allows for the complete cleaning and sterilization of the CMD surgical instrument because there are no tangential surface contacts and sufficiently large cavities, such as cavities having a size that do not facilitate capillary action, present in the CMD rongeur 100.

Referring now to FIGS. 4-10B and 11B, there is illustrated a second example implementation of a CMD surgical instrument. In this implementation, the CMD surgical instrument comprises a CMD kerrison-rongeur 200. The CMD kerrison-rongeur 200 can be formed from two pieces of metal or elastomeric polymer. A traditional kerrison-rongeur surgical instrument typically is formed from at least four separate components, two leaf springs, and several screws. These traditional designs are very difficult to clean after surgeries due to the presence of tangential surface contacts between the separate components and the inner lumen at the rotating axis and other small capillaries surrounding any screw used for assembly of movable joints.

In this implementation, the CMD kerrison-rongeur 200 can comprise a first member 202 and a separate second member 204 with the first and second members 202, 204 configured to be removably coupled. The first member 202 generally comprises an elongated track member 206 having a proximal end 206a and a distal end 206b. The second member 204 generally comprises an elongated cutting slide 208 have a proximal end 208a and a distal end 208b. The elongated track member 206 can comprise a track 210 that extends longitudinally along a length of the elongated track member 206.

Figures 6, 7A, 7B:
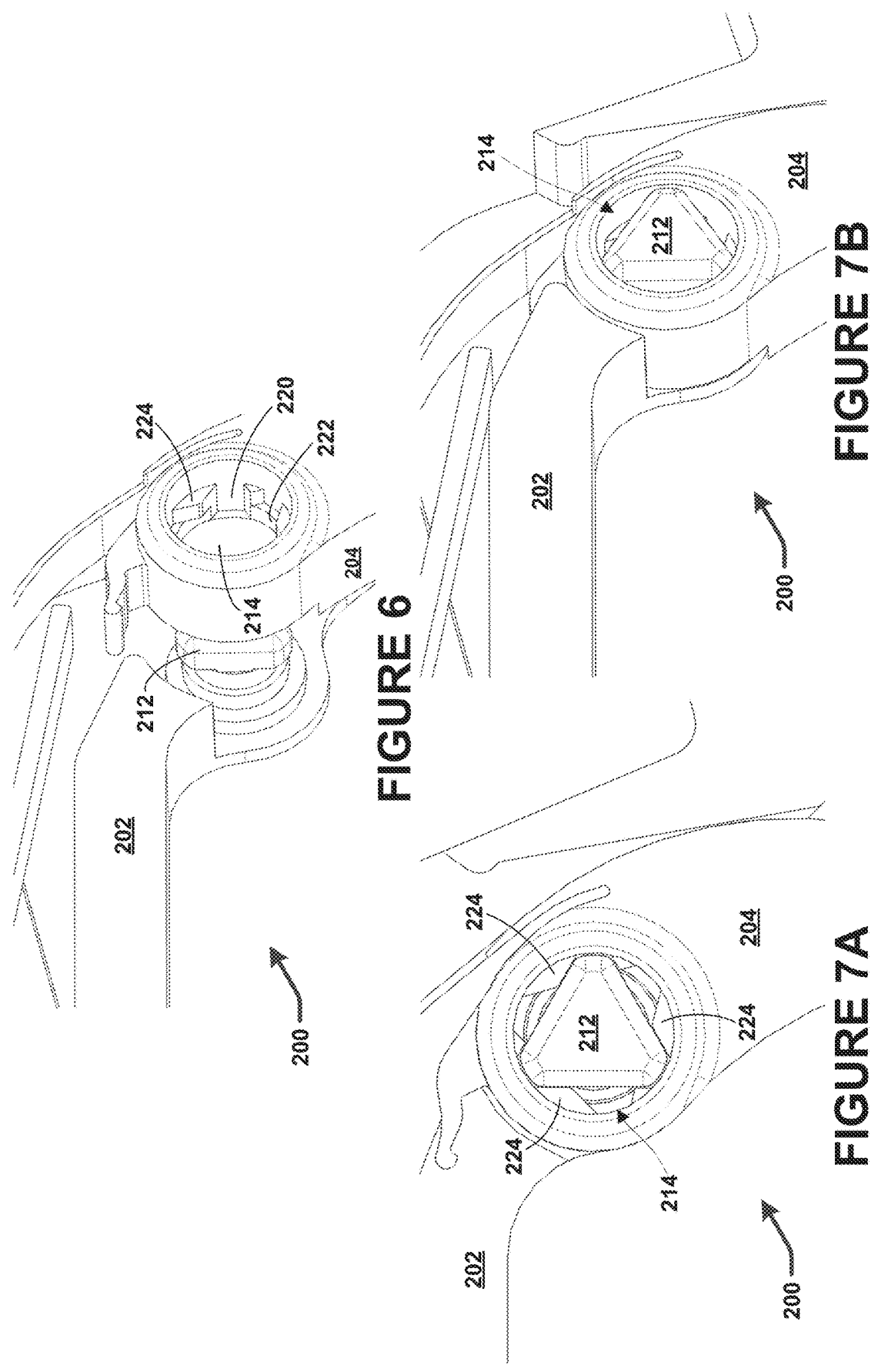
FIG. 6 is a component diagram illustrating one or more portions of the CMD surgical instrument of FIG. 4.
FIGS. 7A and 7B are component diagrams illustrating one or more portions of the CMD surgical instrument of FIG. 4 during assembly.

The first member 202 further comprises a boss 212 that is configured to be mated with a hole 214 disposed in the second member 204 by slidably inserting the boss 212 into the hole 214, as represented by A. The boss 212 can be disposed adjacent the proximal end 206a of the track member 206 where the track member 206 terminates in a handle 216 as described in detail below. The boss 212 can be any suitable size and shape that permits the boss 212 to be slidably inserted into, and mated with, the complementary hole 214 of the second member 204. In some implementations, the boss 212 comprises a triangular shaped protrusion configured to be mated with a hole 214 of specific internal shape in the second member 204 by slidably inserting the boss 212 into the hole 214, as shown in FIG. 6.

Figures 5A, 5B:
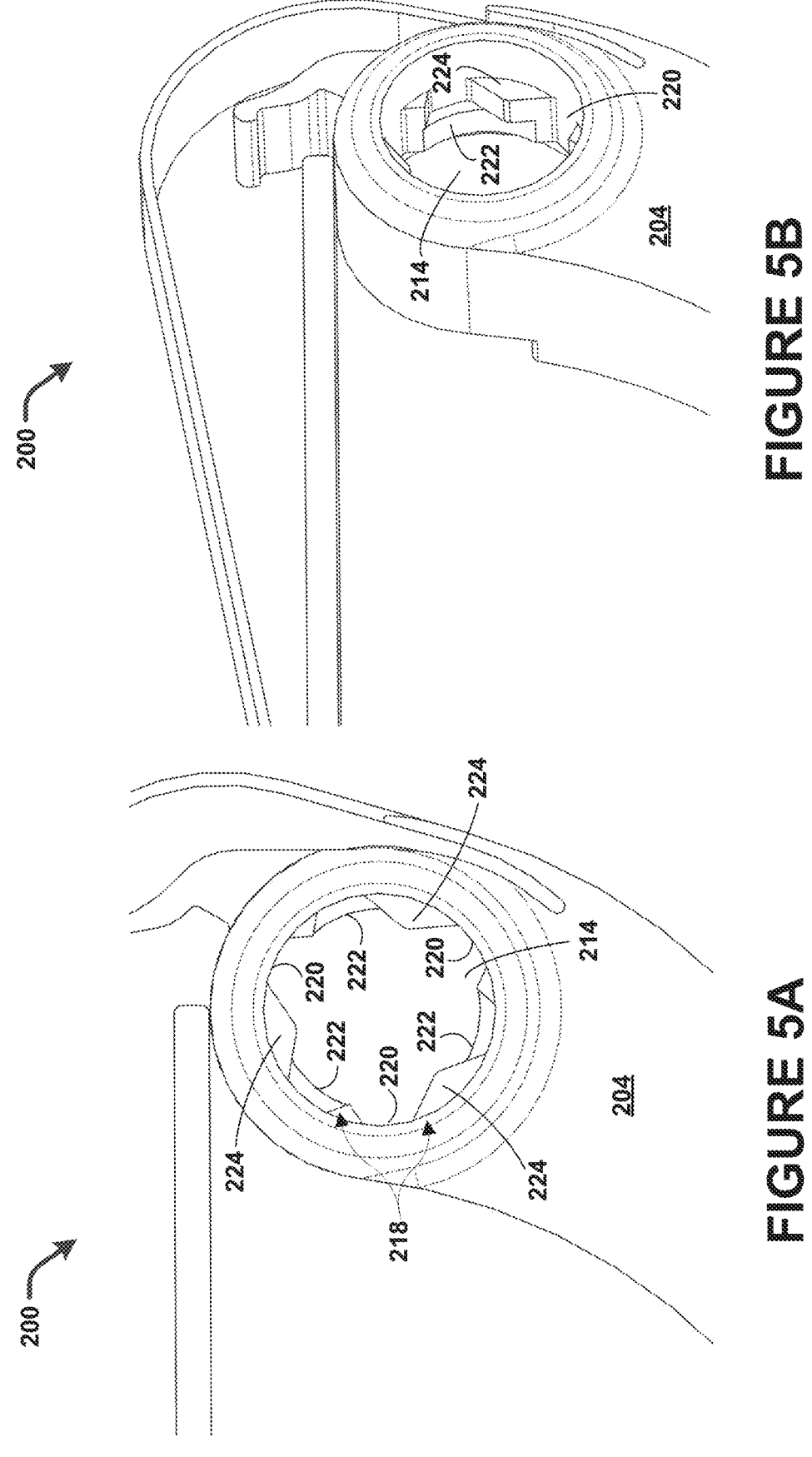
FIGS. 5A and 5B are component diagrams illustrating one or more portions of the CMD surgical instrument of FIG. 4.

The second member 204 can comprise a plurality of boss-engaging features 218 disposed in the hole 214, as shown in FIGS. 5A and 5B. The boss-engaging features 218, such as recessed shelves 222, shelves 224, and slots 220, are configured to selectably engage the boss 212 in order to removably couple the first member 202 to the second member 204 when the boss 212 is inserted into the hole 214. In this implementation, the boss-engaging features 218 form a three-way lock.

The second member 204 can comprise a plurality of slots 220 disposed in the hole 214. The slots are formed in the walls of the second member 204 that define the hole 214. The slots 220 can extend the length of the hole 214 (i.e., all the way through the hole 214) from one side of the second member 204 to the other side. As an example, the hole 214 can comprise three slots 220 that are configured to permit the triangular-shaped boss 212 of the first member 202 to be slidably inserted into the hole 214 when the three vertices of the triangular boss 212 are aligned with the complementary slots 220 in the hole 214.

The second member 204 can further comprise a plurality of recessed shelves 222 disposed in the hole 214. The recessed shelves 222 extend radially inward from the walls of the second member 204 that define the hole 214. As an example, the second member 204 can comprise three recessed shelves 222 that are disposed in the hole 214 and configured to permit the second member 204 to move forward relative to the first member 202 to create a gap 226 between the first member 202 and the second member 204. The three recessed shelves 222 act as a stop to prevent further relative movement of the first and second members 202, 204 and expose the gap 226. The gap 226 between the first and second members 202, 204 is large enough in size so as to avoid forming a cavity that promotes capillary action. In this implementation, the gap 226 between the first and second members 202, 204 is greater than 0.5 mm but no more than 2.0 mm in size to maintain structural stability.

The second member 204 can further comprise a plurality of shelves 224 disposed in the hole 214. The shelves 224 extend radially inward from the walls of the second member 204 that define the hole 214. As an example, the hole can comprise three shelves that are configured to maintain engagement between the second member 204 and the first member 202 during use of the surgical instrument. As an example, the first and second members 202 and 204 are maintained in close contact during surgical use.

The cutting slide 208 of the second member 204 is configured to selectably engage the elongated track member 206 when the first and second members 202, 204 are removably coupled. In some implementations, the track 210 is configured to slidably receive the elongated cutting slide 208 which extends approximately the length of the elongated track member 206. In these implementations, the elongated cutting slide 208 is removably attached to the elongated track member 206. It will be appreciated that any method of fixedly but removably interconnecting the elongated cutting slide 208 of the second member 204 with the elongated track member 206 of the first member 202 in a pivoting, sliding relationship may be utilized in accordance with this disclosure.

In this implementation, the distal end 206b of the elongated track member 206 terminates in a first jaw 228 which extends upwardly from the elongated track member 206 in the distal direction at a desired angle. In some implementations, the first jaw 228 extends upwardly from, and approximately perpendicularly to, the elongated track member 206. The distal end 208b of the elongated cutting slide 208 terminates in a second jaw 230 which extends downwardly from the elongated cutting slide 208 and is configured to selectively engage with the first jaw 228. The first jaw 228 may extend upwardly for a length approximately equal to the height of the distal end 208b of the elongated cutting slide 208. The first jaw 228 may be of any thickness sufficient to withstand the force exerted by the advancement of the elongated cutting slide 208 against the first jaw 228. During surgical use, the first and second jaws 228, 230 of the first and second members 202, 204 cooperate to cut bone and/or tissue of a patient.

The first member 202 and the second member 204 each comprise a handle 216, 232 respectively. For the first member 202, the proximal end 206a of the elongated track member 206 terminates in the handle 216 that extends downwardly from the elongated track member 206 in the proximal direction at a desired angle. For the second member 204, the proximal end 208a of the elongated cutting slide 208 terminates in the handle 232 that extends downwardly from the elongated cutting slide 208 in the distal direction at a desired angle.

In this implementation, the handles 216, 232 of the respective first and second members 202, 204 may biased away from each other by biasing members 234, 236. The biasing members 234, 236 each have a top end and a bottom end. The bottom end of first biasing member 234 is integrally formed to the bottom end of the handle 216. The bottom end of the second biasing 236 member is integrally formed to the bottom end of the second handle 232. The top ends of the biasing members 234, 236 include means to interlock the two biasing members 234, 236. When the biasing members 234, 236 are interlocked, they are biased away from each other, thereby biasing the handle 232 distally. Any suitable means may be used to interlock the two biasing members 234, 236. As an example, one biasing member 236 may include a tab 238 or other protrusion at its top end that fits into a notch 240 in the top end of the other biasing member 234.

FIGS. 6 through 10B illustrate the assembly of the CMD kerrison-rongeur 200. The first member 202 is removably coupled to the second member 204 by selectably inserting the boss 212 into the hole 214. In this implementation, the hole 214 comprises three slots 220 that complement the triangular-shaped boss 212 and facilitate insertion of the boss 212 into the hole 214 when the three vertices of the triangular boss 212 are aligned with the three complementary slots 220 in the hole 214, as shown in FIG. 6. The slots 220 help advance the boss 212 through the hole 214. In this implementation, the second member 204 is in an extreme squeezed position during insertion. As shown in FIG. 10A, the second member 204 and first member 202 are pushed together, as represented by arrow B, until the handle 232 of the second member 204 is disposed in contact with the handle 216 of the first member 202. Before releasing the handle 232 of the second member 204 from the handle 216 of the first member 202, the most proximal portion 208c of the cutting slide 208 is placed inside a catch 208d, as shown in FIG. 10A, and the distal portion 208b of cutting slide 208 is pushed down onto the distal end 206b of track member 206 as indicated by arrow C. As the handle 232 of the second member 204 is released the long upper tension band pushes the distal portion of the cutting slide 208 of the second member 204 forward and urges the CMD kerrison-rongeur 200 towards a surgical use ready position. As shown in FIGS. 7A and 8A, rotation of the second member 204 relative to the first member 202 causes the boss 212 to undergo corresponding rotation within in the hole 214 such that the second member 204 enters a normal position or operating configuration. FIG. 8A shows the hole 214 rotated in such position that the shelves 224 maintain the first and second members 202, 204 in surgical use position. FIG. 10A shows the CMD kerrison-rongeur 200 having a pistol-grip styled shape with first and second members 202, 204 removably coupled and the biasing members 234 and 236 have interlocked their tab 238 and notch 240.

Figures 8A, 8B:
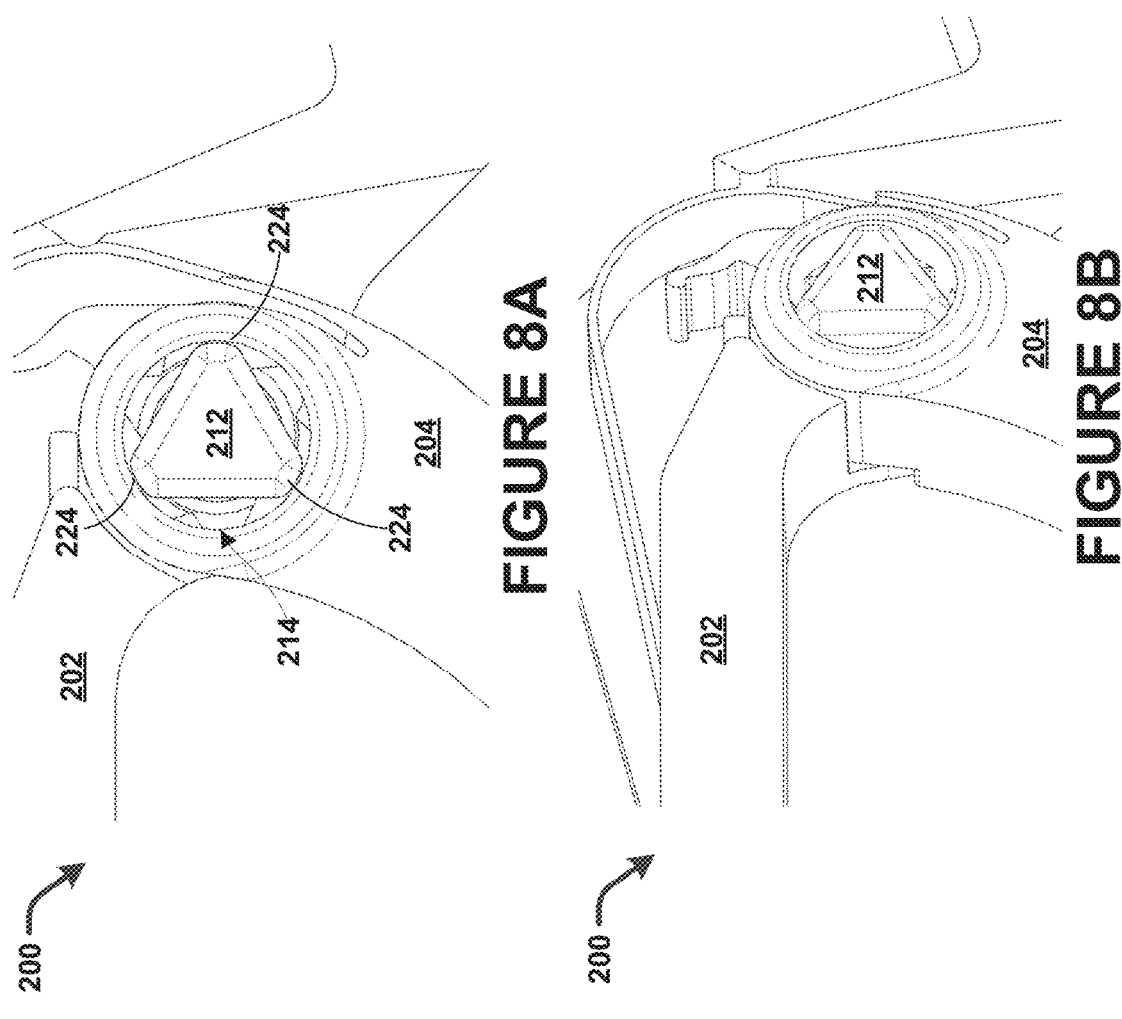
FIGS. 8A and 8B are component diagrams illustrating one or more portions of the CMD surgical instrument of FIG. 4 as configured during surgical use.

FIGS. 8A and 8B show the CMD kerrison-rongeur 200 during surgical use. During surgical use, the handles 216, 232 are squeezed together which causes the cutting slide 208 of the second member 204 to slide forward in the distal direction relative to the track member 210 of the first member 202. In particular, squeezing the handles 216, 232 causes the jaw 230 of the cutting slide 208 to move towards the jaw 228 of the track member 206 for cutting tissue at the tip.

During surgical use of the CMD kerrison-rongeur 200, the boss 212 engages the plurality of shelves 224 disposed within the hole 214. In effect, the boss 212 is captured by the plurality of shelves 224 disposed within the hole thereby preventing the second member 204 from disengaging from the first member 202 and, by extension, preventing decoupling. It will be appreciated from this disclosure that the second member 204 and associated elongated cutting slide 208 is free to move "linearly" during surgical use, as shown in part in FIGS. 8A and 8B.

Figures 9A, 9B, 9C:
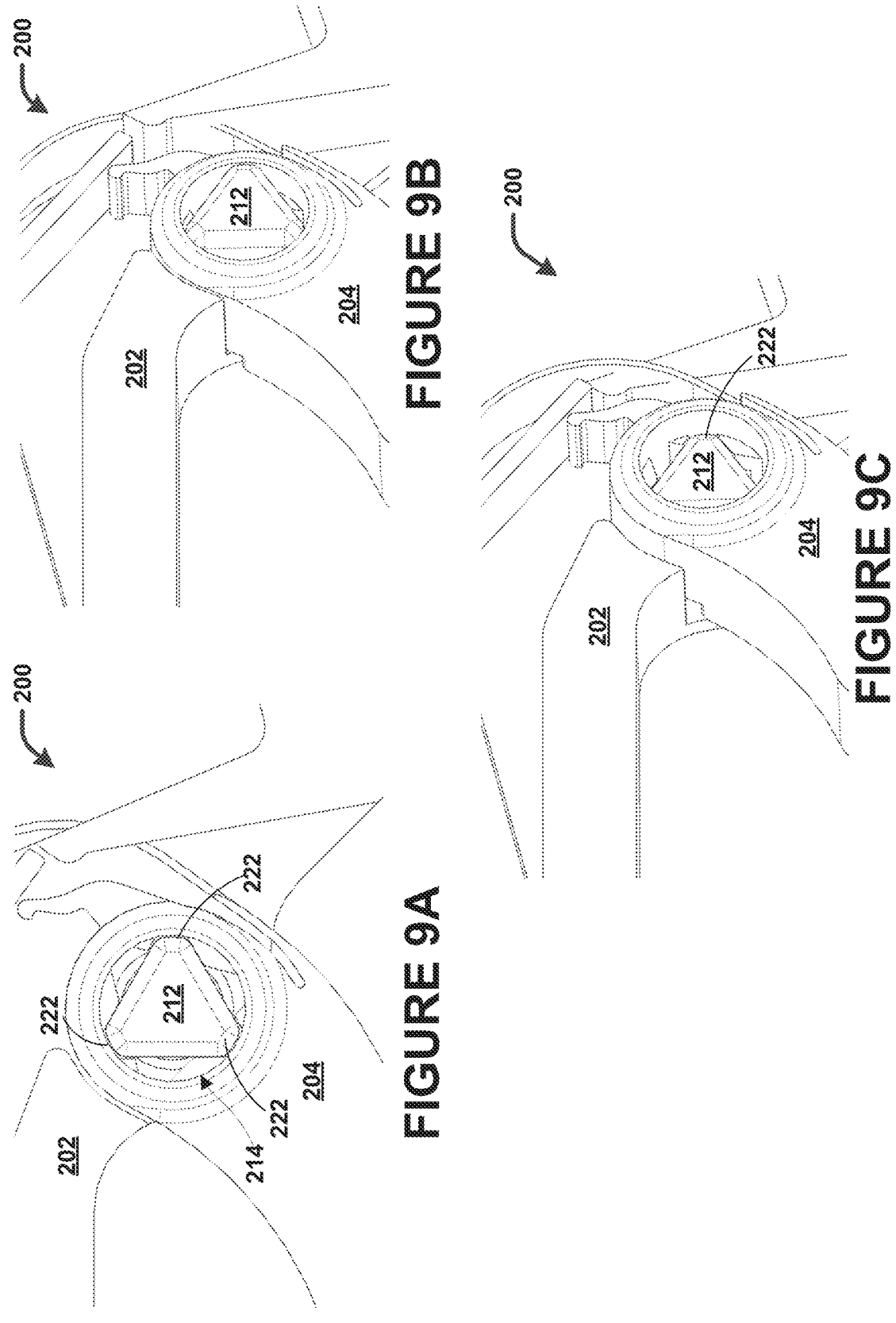
FIGS. 9A, 9B, and 9C are component diagrams illustrating one or more portions of the CMD surgical instrument of FIG. 4 during disassembly.
Figure 10A:
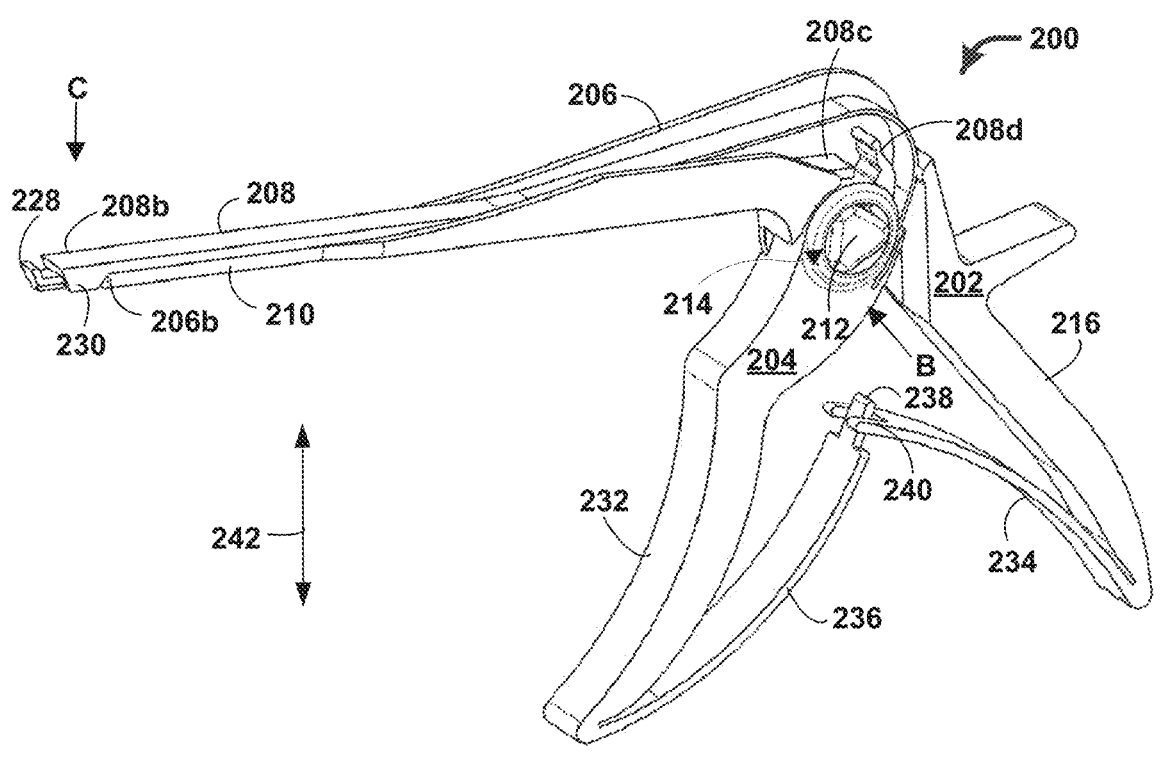
FIG. 10A is a component diagram illustrating the CMD surgical instrument of FIG. 4 in a surgical use or operating configuration.
Figure 10B:
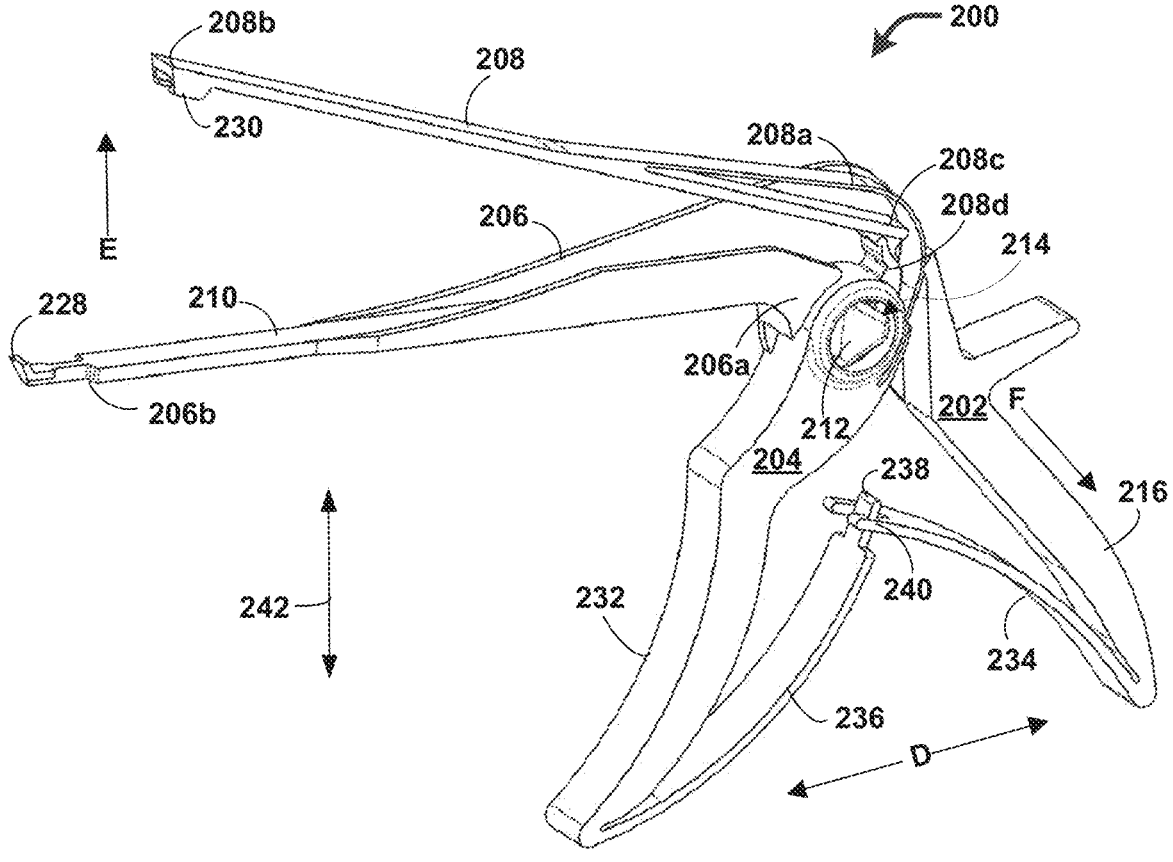
FIG. 10B is a component diagram illustrating the CMD surgical instrument of FIG. 4 in a cleaning configuration.

FIGS. 9A-9C and 10B show the CMD kerrison-rongeur 200 transition from a surgical use or operating configuration, such as that shown in FIG. 10A, to configuration for cleaning, in which the first and second members 202, 204 are disengaged and decoupled, by performing the following sequence of steps. First, the handles 216, 232 are moved apart, as represented by arrow D shown in FIG. 10B, with the handle 232 of the second member 204 opened to its maximum. Pulling the handles 216, 232 apart allows the elongated cutting slide 208 of the second member 204 to spring upward from the track member 206 of the first member 202, as represented by arrow E shown in FIG. 10B, thereby separating the elongated cutting slide 208 from the elongated track member 206. Pulling the handles 216, 232 apart also allows for the second member 204 to be pushed outward in the lateral direction, as represented by arrow F in FIG. 10B, thereby forming a gap 226 between the first and second members 202, 204. This action can be performed by the person performing the cleaning or it can be done by an internal spring (not shown) between first member 202 and second member 204 around the central axis of boss 212.

Figures 11A, 11B:
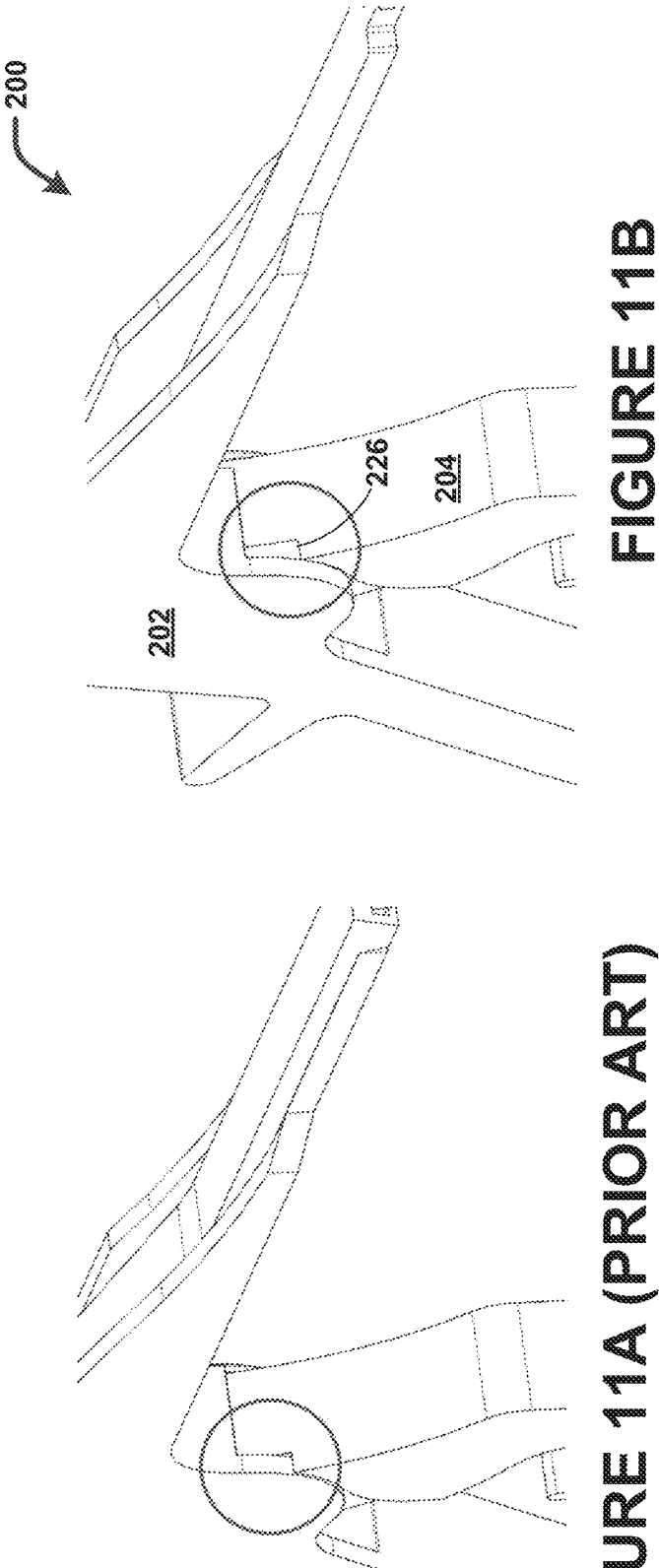
FIG. 11A is a component diagram illustrating one or more portions of the prior art for comparison to FIG. 11B.
FIG. 11B is a component diagram illustrating a gap in one or more portions of the CMD surgical instrument of FIG. 4 in accordance with this disclosure.

With respect to the gap 226, the movement described above aligns the vertices of the triangular boss 212 with the plurality of recessed shelves 222 disposed within the hole 214, as shown in FIGS. 9A through 9C. This permits the second member 204 to slide outward, or laterally, by at least 2.0 mm to create the gap 226, as shown in FIG. 11B. The gap 226 is a large cavity that promotes complete rinsing, cleaning, and sterilization of the CMD kerrison-rongeur 200 without any undesirable capillary action.

Traditional kerrison-rongeur surgical instruments do not permit such movement between components to form a gap. FIG. 11A depicts a traditional or existing kerrison-rongeur surgical instrument which does not provide for a gap. Additionally, some existing kerrison-rongeur surgical instruments do not allow for the cutting slide to disengage from the track member to form a space (e.g., lumen) therebetween. As a result, existing kerrison-rongeur surgical instruments are difficult to properly clean after use.

Figure 12:
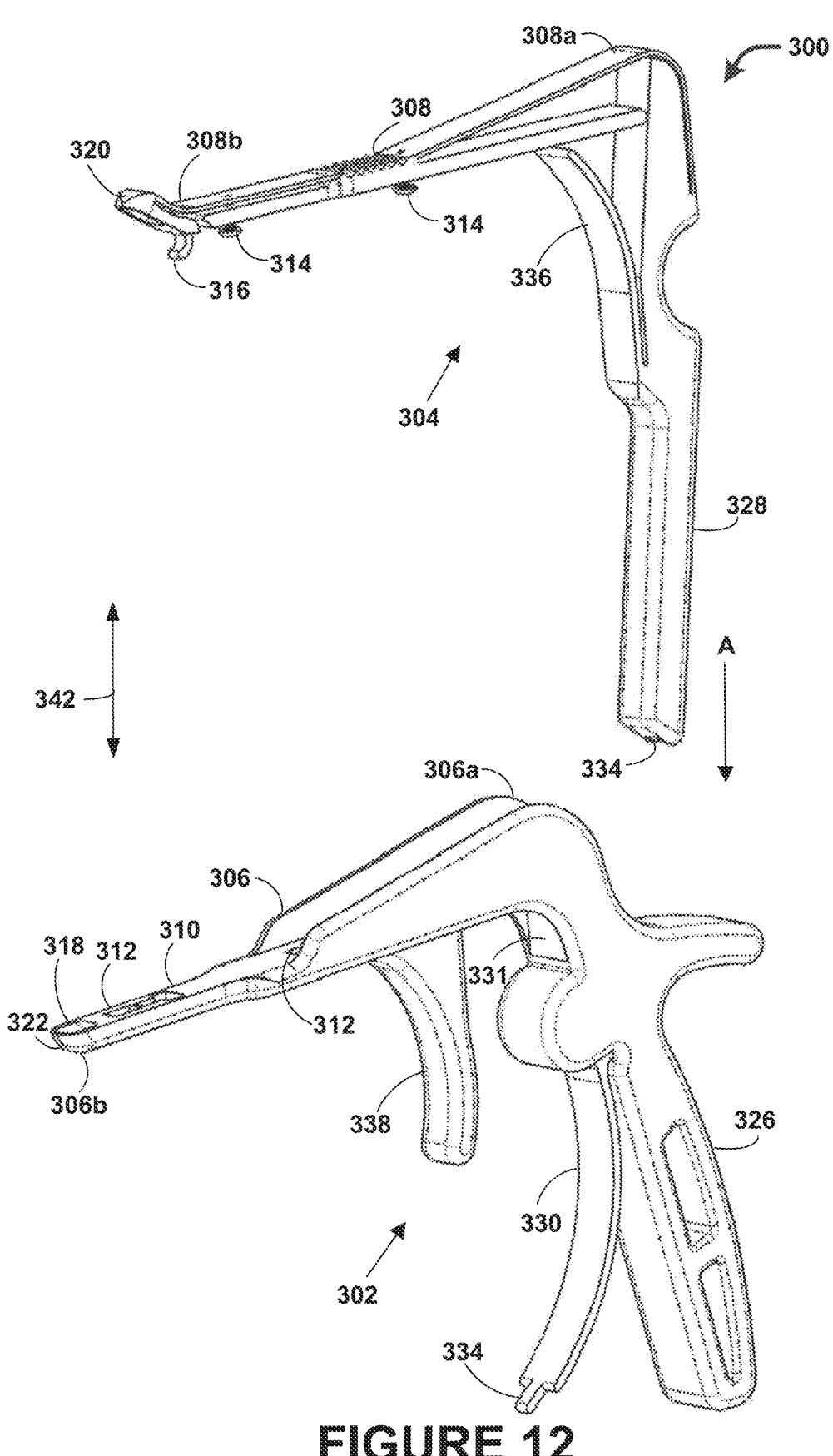
FIG. 12 is a component diagram illustrating another example implementation of a CMD surgical instrument in accordance with this disclosure.
Figures 13, 14:
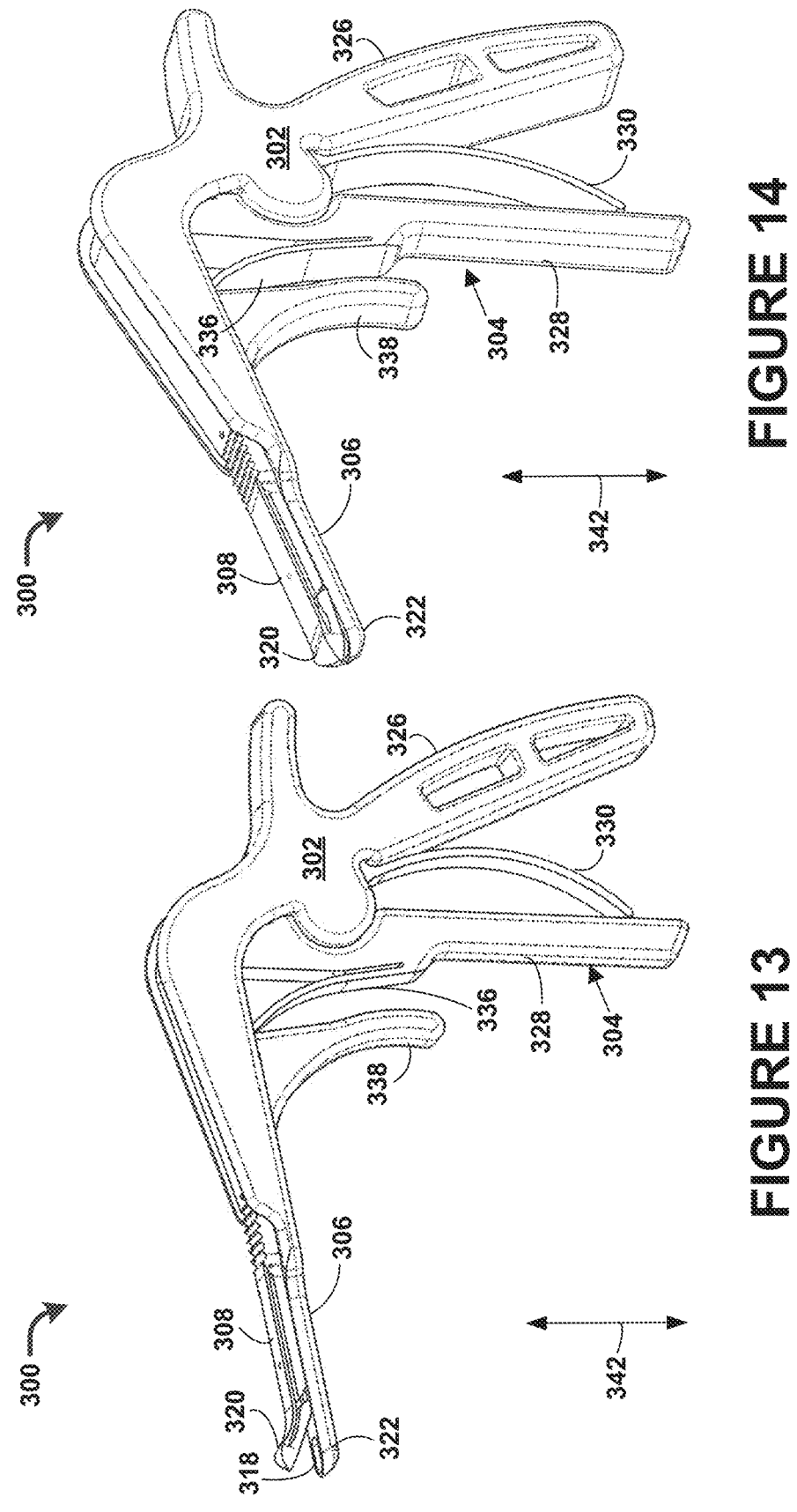
FIG. 13 is a component diagram illustrating the CMD surgical instrument of FIG. 12 in a ready-for-use surgical position.
FIG. 14 is a component diagram illustrating the CMD surgical instrument of FIG. 12 in an actuated condition.

Referring now to FIGS. 12 through 14, there is illustrated another example implementation of a CMD surgical instrument. In this implementation, the CMD surgical instrument comprises a CMD kerrison-pituitary 300. The CMD kerrison-pituitary 300 can be formed from two pieces of metal or elastomeric polymer. A traditional kerrison-pituitary surgical instrument typically is formed from at least four separate components, two leaf springs, and several screws. These traditional designs are very difficult to clean after surgeries due to the presence of tangential surface contacts between the ties connecting the separate components and the rotating axis.

In this implementation, the CMD kerrison-pituitary 300 can comprise a first member 302 and a separate second member 304 with the first and second members 302, 304 configured to be removably coupled. The first member 302 generally comprises an elongated track member 206 having a proximal end 306a and a distal end 306b. The second member 304 generally comprises an elongated cutting slide 308 have a proximal end 308a and a distal end 308b. The elongated track member 306 has a plurality of openings 312 that are each configured to receive a protrusion 314 disposed on the elongated cutting slide 308 as described in more detail below. The elongated track member 306 has a receiving slot 318 that is configured to receive a curved engaging member 316 disposed on the elongated cutting slide 308 as described in more detail below.

The elongated cutting slide 308 comprises a plurality of protrusions 314 disposed between the proximal and distal end 308a, 308b of the elongated cutting slide 308. The plurality of protrusions 314 are configured to be mated with the plurality of openings 312 of the elongated track member 306 by selectably inserting the protrusions into complementary openings 312 disposed on the first member 302. As an example, the elongated cutting slide 308 can comprise first and second protrusions 314 that are each disposed on the bottom side of the elongated cutting slide 308 and are spaced apart by some distance selected to match the spacing arrangement of the complementary openings 312 to facilitate mating. But, it will be appreciated from this disclosure that any number of protrusions and corresponding openings can be used.

The first and second protrusions 314 have a size, shape, and spacing arrangement that permits the protrusions 314 to be selectably inserted into, and mated with, complementary first and second openings 312 disposed in the elongated track member 306. In some implementations, the protrusions 314 comprise circular tabs configured to be slidably inserted into, and mated with, circular openings 312 in the first member 302 by slidably inserting the protrusions 314 into the openings 312.

The second member 304 further comprises a curved engaging member 316 disposed on the bottom side of the elongated cutting slide 308. The curved engaging member 316 is configured to be mated with a corresponding receiving slot 318 disposed in the elongated track member 306 of the first member 302 by inserting the curved engaging member 316 into the receiving slot 318. The curvature of the curved engaging member 316 limits movement of the curved engaging member 316 when mated with the receiving slot 318. The curved engaging member 316 can be disposed adjacent a jaw 320 disposed at the distal end 308a of the cutting slide 308. In this implementation, the curved engaging member 316 is disposed between the jaw 320 and the first and second protrusions 314. The curved engaging member 316 can be any suitable size and shape that permits the curved engaging member 316 to be inserted into, and mated with, the complementary receiving slot 318 of the first member 302.

The cutting slide 308 of the second member 304 is configured to selectably engage the elongated track member 306 when the first and second members 302, 304 are removably coupled. In some implementations, the track member 306 comprises a track 310 configured to slidably receive the elongated cutting slide 308 which extends approximately the length of the elongated track member 306. In this implementations, the elongated cutting slide 308 is removably attached to the elongated track member 306. It will be appreciated that any method of fixedly but removably interconnecting the elongated cutting slide 308 of the second member 304 with the elongated track member 306 of the first member 302 in a pivoting, sliding relationship may be utilized in accordance with this disclosure.

In this implementation, the distal end 306b of the elongated track member 306 terminates in a jaw 322 and the distal end 308b of the elongated cutting slide terminates in a jaw 320. The jaw 320 is configured to be movable between a first position and second position. When the jaw 320 is in a first position, the jaw 320 is no longer coplanar with the elongated cutting slide 308. In the first position, the jaw 320 extends at an upward angle, in the distal direction, from the elongated cutting slide 308. When the jaw 320 is in a second position, the jaw 320 is coplanar with the elongated cutting slide 308. The jaw 320 may be of any thickness sufficient to withstand the force exerted by the advancement of the elongated cutting slide 208 which causes the jaw 320 to move to the second position and close down on the jaw 322. During surgical use, the jaws 322, 320 of the first and second members 302, 304 cooperate to cut bone and/or tissue of a patient.

The first member 302 and the second member 304 each comprise a handle 326, 328 respectively. For the first member 302, the proximal end 306a of the elongated track member 306 terminates in the handle 326 that extends downwardly from the elongated track member 306 in the proximal direction at a desired angle. The first member 302 further comprises a resilient member 330 that extends downwardly from the elongated track member 306 and is disposed distal to the handle 326. For the second member 304, the proximal end 308a of the elongated cutting slide 308 terminates in the handle 328 that extends downwardly from the elongated cutting slide 308, approximately perpendicular to a longitudinal axis of the elongated cutting slide 308.

In this implementation, the handles 326, 328 of the respective first and second members 302, 304 may be biased away from each other by the resilient member 330 that is disposed between the handles 326, 328 when the first member 302 is removably coupled to the second member 304. The resilient member 330 has a top and bottom end. The top end is integrally formed with the first member 302. The bottom end can include a tab 332 configured to engage a notch 334 in the handle 328 of the second member 304.

FIG. 12 illustrates the assembly of the CMD kerrison-pituitary 300. The first member 302 is removably coupled to the second member 304 by selectably inserting the handle 328 of the second member 304 into an aperture 331 in the first member 302 such that the handle 328 is disposed distal to the resilient member 330 and handle 328 with the resilient member 330 disposed between the handles 326, 328. Inserting the handle 328 into the aperture 331 is accompanied by inserting the plurality of protrusions 314, or tabs, into complementary openings 312 disposed in the elongated track member 306. Inserting the handle 328 into the aperture 331 is further accompanied by inserting the curved engaging member 316 into the receiving slot 318 of the elongated track member 306. Once mating of the protrusions 314 with the complementary openings 312 and mating of the curved engaging member 316 with the receiving slot 318 are complete, the CMD kerrison-pituitary 300 is ready for operation.

FIG. 13 shows the CMD kerrison-pituitary 300 in ready for surgical use condition, while FIG. 14 shows the fully actuated condition (biting into tissue). During operational use, the handles 326, 328 are squeezed together thereby causing the elongated cutting slide 308 of the second member 304 to slide forward relative to the elongated track member 306. Due to the interaction of the curved engaging member 316 and the receiving slot 318, the jaw 320 moves/rotates from the first position (e.g., open or raised position), as shown in FIG. 13, to the second position (e.g., closed), as shown in FIG. 14. In the second position, the jaws 320, 322 are closed together.

To disassemble the CMD kerrison-pituitary 300 for cleaning and sterilization, the second member 304 can be pulled vertically upwards and away from the first member 302. As one example, the first and second members 302, 304 are disengaged and decoupled, by performing the following sequence of steps. First, the handles 326, 328 are moved apart, with the handle 326 of the second member 304 opened to its maximum. Pulling the handles 326, 328 apart allows the elongated cutting slide 308 of the second member 304 to spring upward from the tracking member 306 of the first member 302. The second member 304 can now be completely removed from the first member 302 and both portions can be independently cleaned and sterilized.

Referring now to FIGS. 15 through 18, there is illustrated another example implementation of a CMD surgical instrument 400. In this implementation, the CMD surgical instrument comprises a CMD French bender spreader mechanism 400 (hereinafter referred to as CMD French bender 400), which is a single hinge point mechanism. The CMD French bender 400 can be formed from one piece of metal or elastomeric polymer plus eight rollers and two bend plates 403.

A traditional French bender surgical instrument typically is formed from at least twelve separate components and has multiple rotating axis. These traditional designs are very difficult to clean after surgeries due to the presence of tangential surface contacts and thin, inner lumen around the rotating axis.

Figures 15A, 15B, 15C:
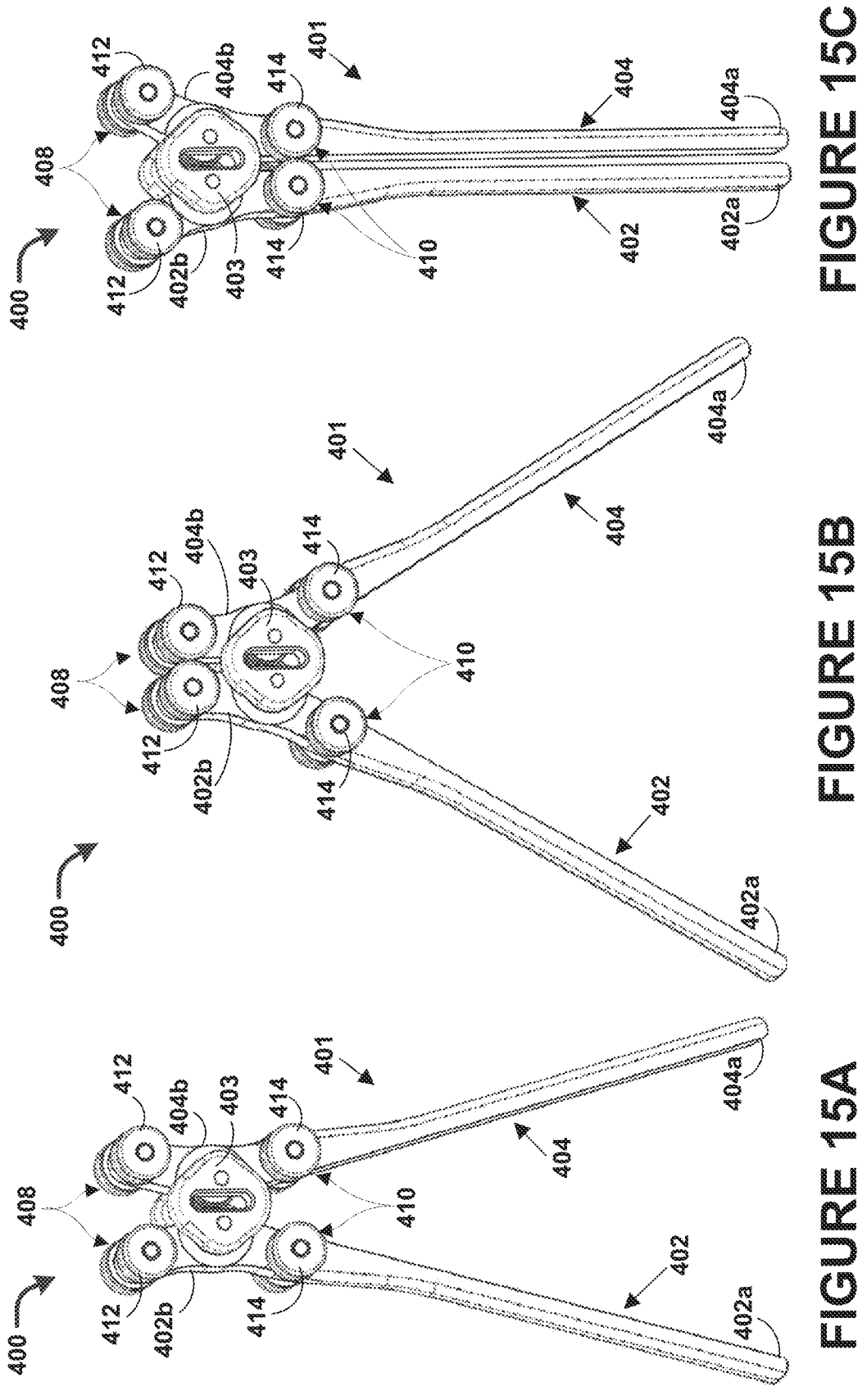
FIGS. 15A through 15C are component diagrams illustrating another example implementation of a CMD surgical instrument in accordance with this disclosure.

FIGS. 15A through 15C illustrate the CMD French bender 400 in three positions or configurations. FIG. 15A shows the CMD French bender 400 in a neutral position or rest position. The CMD French bender 400 can be moved to an open position, as shown in FIG. 15B, and to a closed position, as shown in FIG. 15C.

In this implementation, the CMD French bender 400 comprises a body 401 and a removably attachable bending plate 403 for bending spinal rods, as shown in FIGS. 16 and 17.

The body 401 can comprise a first member 402, having a proximal end 402a and a distal end 402b, and a second member 404, having a proximal end 404a and a distal end 404b. The proximal ends 402a, 404a of the first and second members 402, 404 act as handles that can be manipulated to cause the CMD French bender 400 to move to the open position, as shown in FIG. 15B, or to the closed position, as shown in FIG. 15C. The distal end 402b, 404b comprises a rolling joint 406 disposed between an upper bend zone 408 and a lower bend zone 410.

The upper bend zone 408 comprises four circular protrusions 412 either as separate rollers or integrally formed with the body 401. The circular protrusions 412 are arranged with one circular protrusion on each of the front and back sides of the first member 402 and one circular protrusion on each of the front and back sides of the second member 404. The front side circular protrusions 412 of the upper bend zone 408 form a spinal rod bending pair. The back side circular protrusions 412 of the upper bend zone 408 form another spinal rod bending pair that may be configured for bending rods of a different size (e.g., bend radii) than the front side circular protrusions of the upper bend zone 408 and/or the lower bend zone 410 as described in more detail below.

Similarly the lower bend zone 410 comprises four circular protrusions 414 also either as separate rollers or integrally formed with the body 401. The circular protrusions 414 are arranged with one circular protrusion on each of the front and back sides of the first member 402 and one circular protrusion on each of the front and back sides of the second member 404. The front side circular protrusions 414 of the lower bend zone 410 form a spinal rod bending pair. The back side circular protrusions 414 of the lower bend zone 410 form another spinal rod bending pair that may be configured for bending rods of a different size (e.g., bend radii) than the front side circular protrusions of the lower bend zone 410 and/or the upper bend zone 408 as described in more detail below.

In this implementation, the rolling joint 406 can comprise a first rolling joint member 416 disposed on the first member 402, a second rolling joint member 418 disposed on the second member 404, and a plurality of resilient bands 420 extending between the first and second members 402, 404. The resilient bands 420 are integrally formed with the first and second members 402, 404. In this manner, the body 401 can be integrally formed from a single sheet of metal and comprise first and second members 402, 404, circular protrusions 412, 414, and the rolling joint 406 which are interconnected via the plurality of resilient bands 420.

Figure 18:
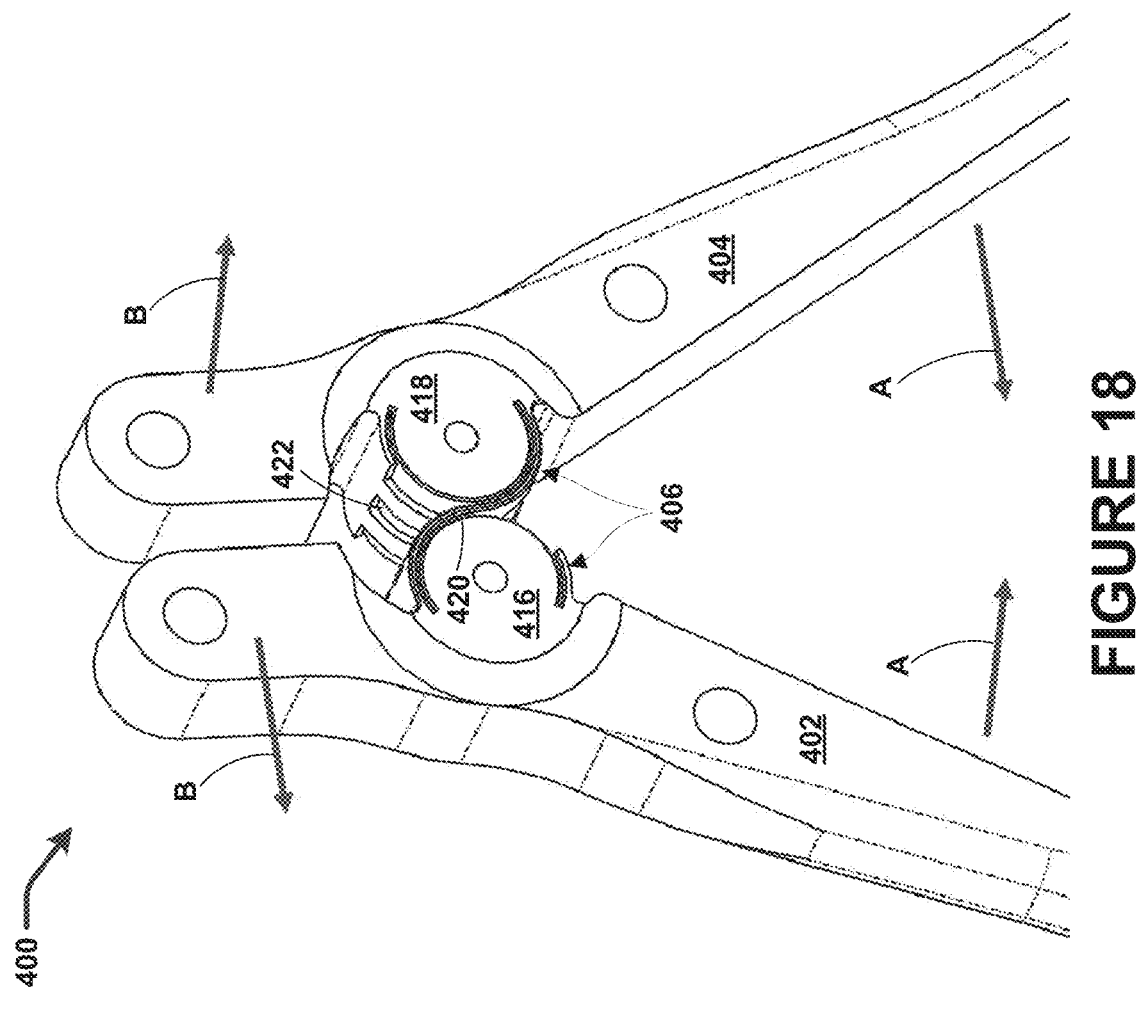
FIG. 18 is a component diagram illustrating one or more portions of the CMD surgical instrument of FIGS. 15A-15C.

The resilient bands 420 are connected to the first member 402 at one end of the band 420 and to the second member 404 at the other end of the band 420. In this implementation, some bands 420 have one end connected to the first member 402 above the first rolling joint member 416 and the other end connected to the second member 404 below the second rolling joint member 418, as shown in FIG. 18, such that the bands cross over. Other bands 420 have one end connected to the first member 402 below the first rolling joint member 416 and the other end connected to the second member 404 above the second rolling joint member 418, such that the bands cross over. In some implementations, the resilient bands 420 are arranged by alternating the connection sequence provided above. The rolling joint 406 with the resilient bands 420 form the hinge point that facilitates relative movement of the first and second members 402, 404.

The CMD French bender 400 typically has an odd number of resilient bands. An uneven number of resilient bands, such as three, five, seven, etc., may provide additional balance. The resilient bands 420 can be arranged in the rolling joint 406 to have spaces 422 or gaps between each of the plurality of the bands 420 to provide for flexing or elastic bending of the bands 420. The spaces 422 are sized such that any cavities on the CMD French bender 400 are at least 0.3 mm, which means there are not any cavities capable of acting in a capillary nature. Thus, the CMD French bender 400 will not draw biologic fluids into cavities where it is trapped, like traditional French benders, because the CMD French bender 400 of this disclosure can be simply and effectively rinsed, cleaned, and sterilized.

Figure 16B:
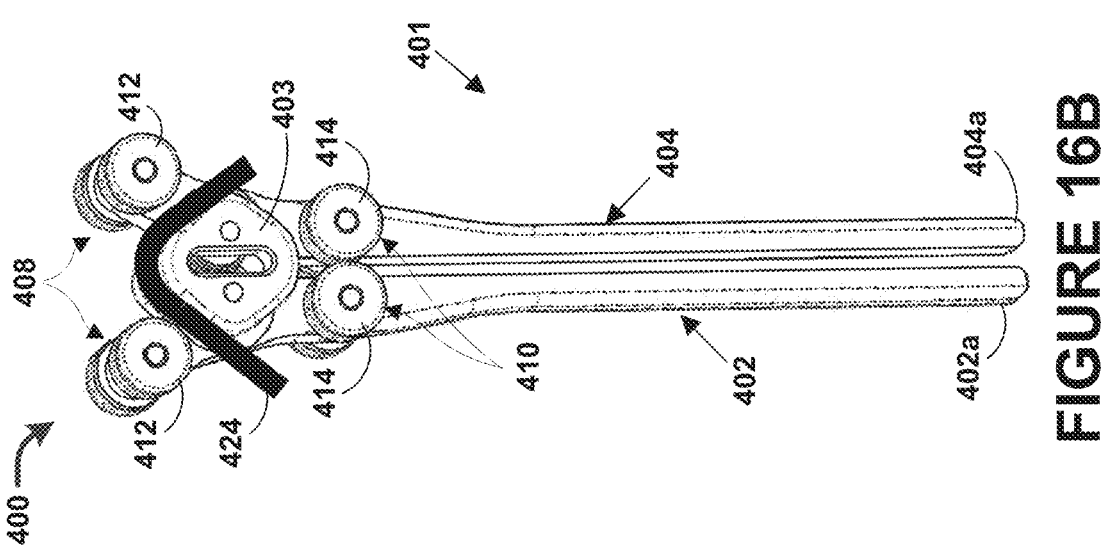
FIGS. 16A and 16B are component diagrams illustrating the CMD surgical instrument of FIGS. 15A-15C being used to bend a spinal rod in an upper bend zone.
Figure 16A:
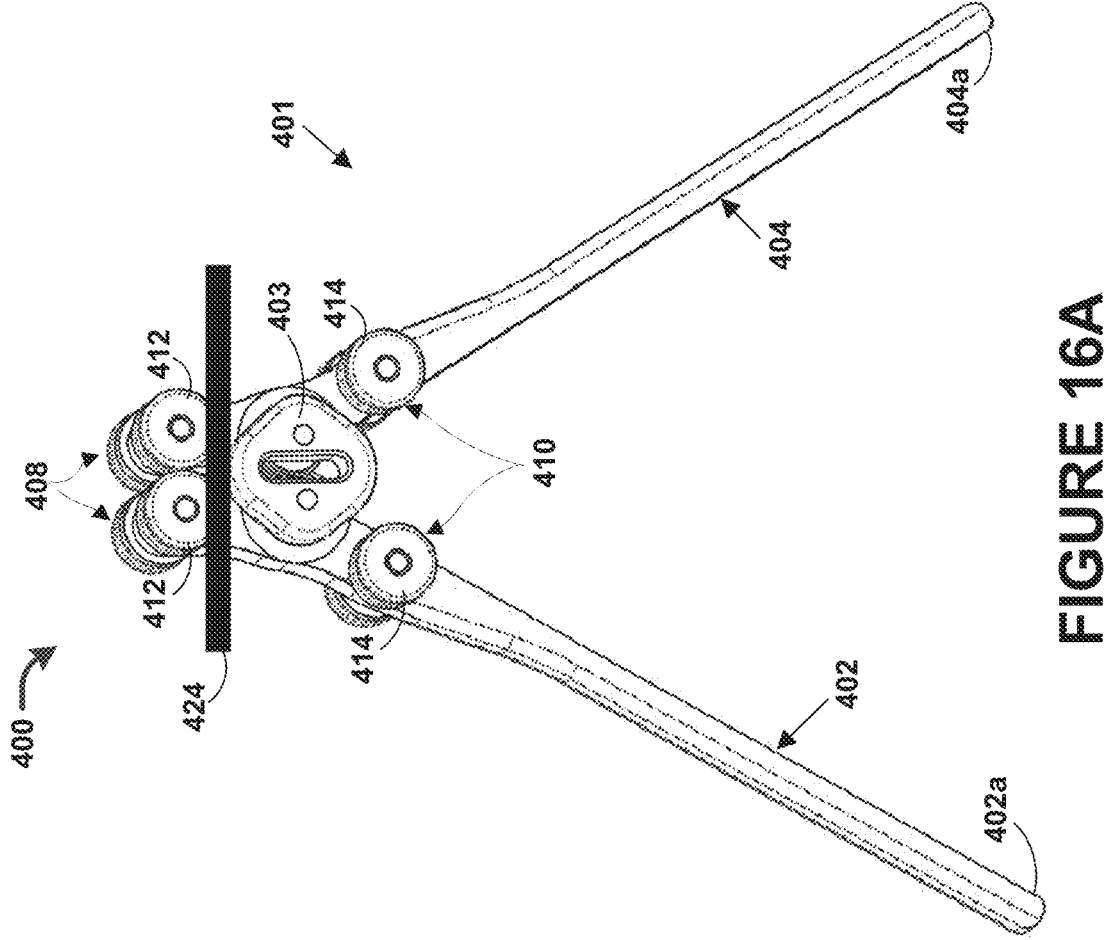

The removably attachable bending plate 403 can be configured to bend spinal rods 424 of at least one size (e.g., bend radii) in the upper bend zone 408 and one size (e.g., bend radii) in the lower bend zone 410. FIG. 16A shows a spinal rod 424 disposed in the upper bend zone 408 between the circular protrusions 412, which are disposed in close contact and potentially touching, and the removably attached bending plate 403. The spinal rod 424 can be inserted into the upper bend zone 408 when the CMD French bender 400 is in the open position. Moving the proximal ends 402a, 404a of the first and second members 402, 404 together to the closed position, as represented by the arrows A in FIG. 18, causes the circular protrusions 412 to move apart, as shown in FIGS. 16B and 18, thereby applying force to the spinal rod 424 in the process. The force applied to the spinal rod 424 by the circular protrusions 412 causes the spinal rod 424 to bend or flex about the bending plate 403 of the upper bend zone 408.

Figures 17A, 17B:
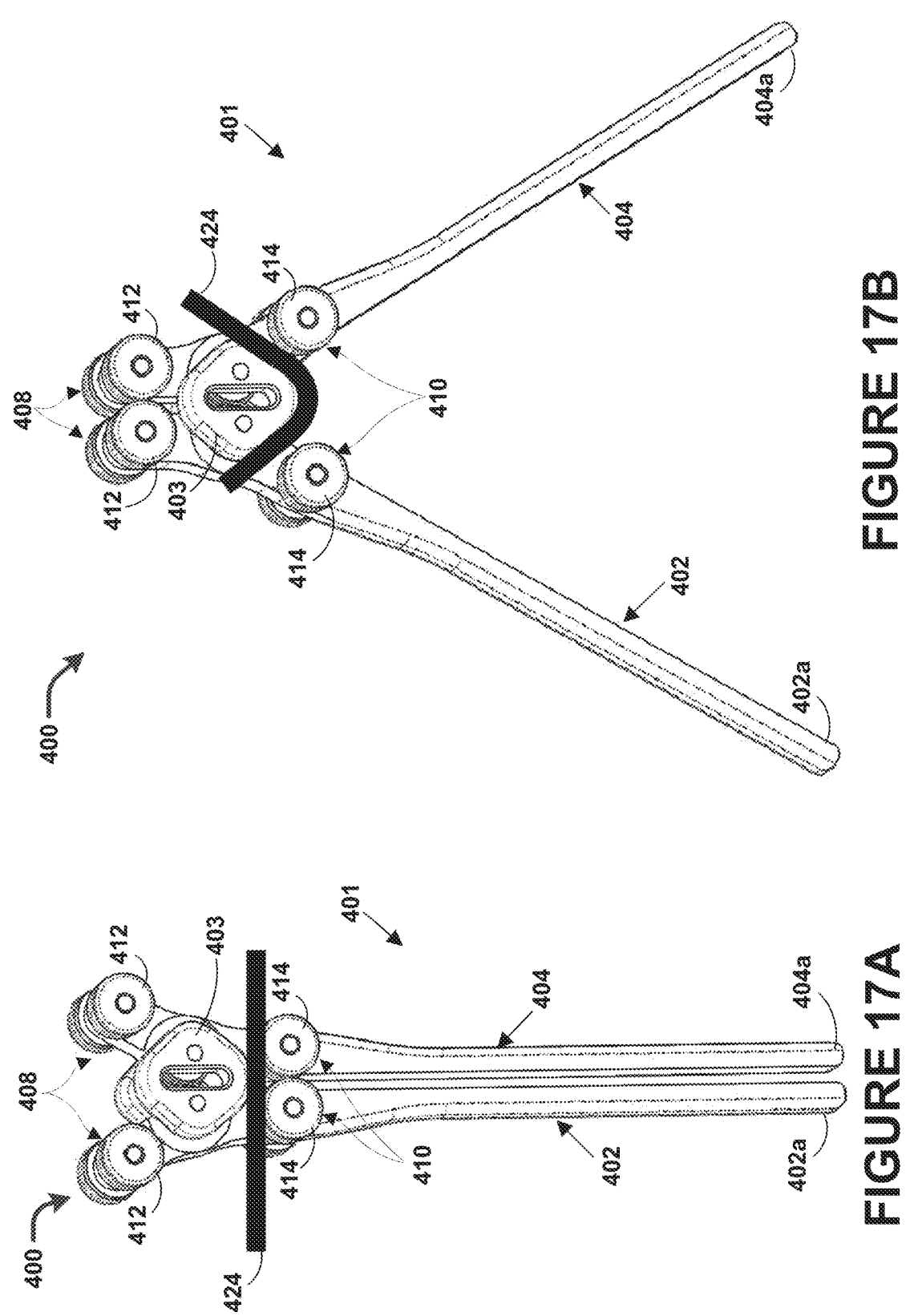
FIGS. 17A and 17B are component diagrams illustrating the CMD surgical instrument of FIGS. 15A-15C being used to bend a spinal rod in a lower bend zone.

FIG. 17A shows a spinal rod 424 disposed in the lower bend zone 410 between the circular protrusions 414, which are disposed in close contact and potentially touching, and the removably attached bending plate 403. The spinal rod 424 can be inserted into the lower bend zone 410 when the CMD French bender 400 is in the closed position. Moving the proximal ends 402a, 404a of the first and second members 402, 404 apart to the open position causes the circular protrusions 414 to move apart, as shown in FIG. 17B, thereby applying force to the spinal rod 424 in the process. The force applied to the spinal rod 424 by the circular protrusions 414 causes the spinal rod 424 to bend or flex about the bending plate 403 of the lower bend zone 410. In some implementations, the bending plate 403 is configured to bend different radii of spinal rods on the front and back such that the bending plate 403 may be configured for four different sizes (e.g., bend radii) of spinal rods—two different bend radii in each upper bend zone 408 and two different bend radii in each lower bend zone 410.

Referring now to FIGS. 19 through 25, there are illustrated several implementations of CMD surgical instruments that each comprise a single hinge point mechanism with a single hinge point. These CMD surgical instruments can comprise scissors, pliers, forceps, and spreaders (or distractors). Each of these CMD surgical instruments can be formed from a single piece or sheet of metal or elastomeric polymer unlike traditional versions of these surgical instruments that have two ties or connections points and one axis for rotation. Due to their design, traditional versions of the scissors, pliers, forceps, and spreaders (or distractors) are very difficult to clean after surgeries because of the presence of tangential surface contacts between ties and the thin lumen surrounding the rotating axis.

Referring now to FIGS. 19 through 22, there is illustrated an example implementation of a CMD surgical instrument. In this example implementation, the CMD surgical instrument is a pair of CMD forceps 500, in particular a rod inserter. The CMD forceps can be formed from a single piece or sheet of metal or elastomeric polymer.

Figure 19:
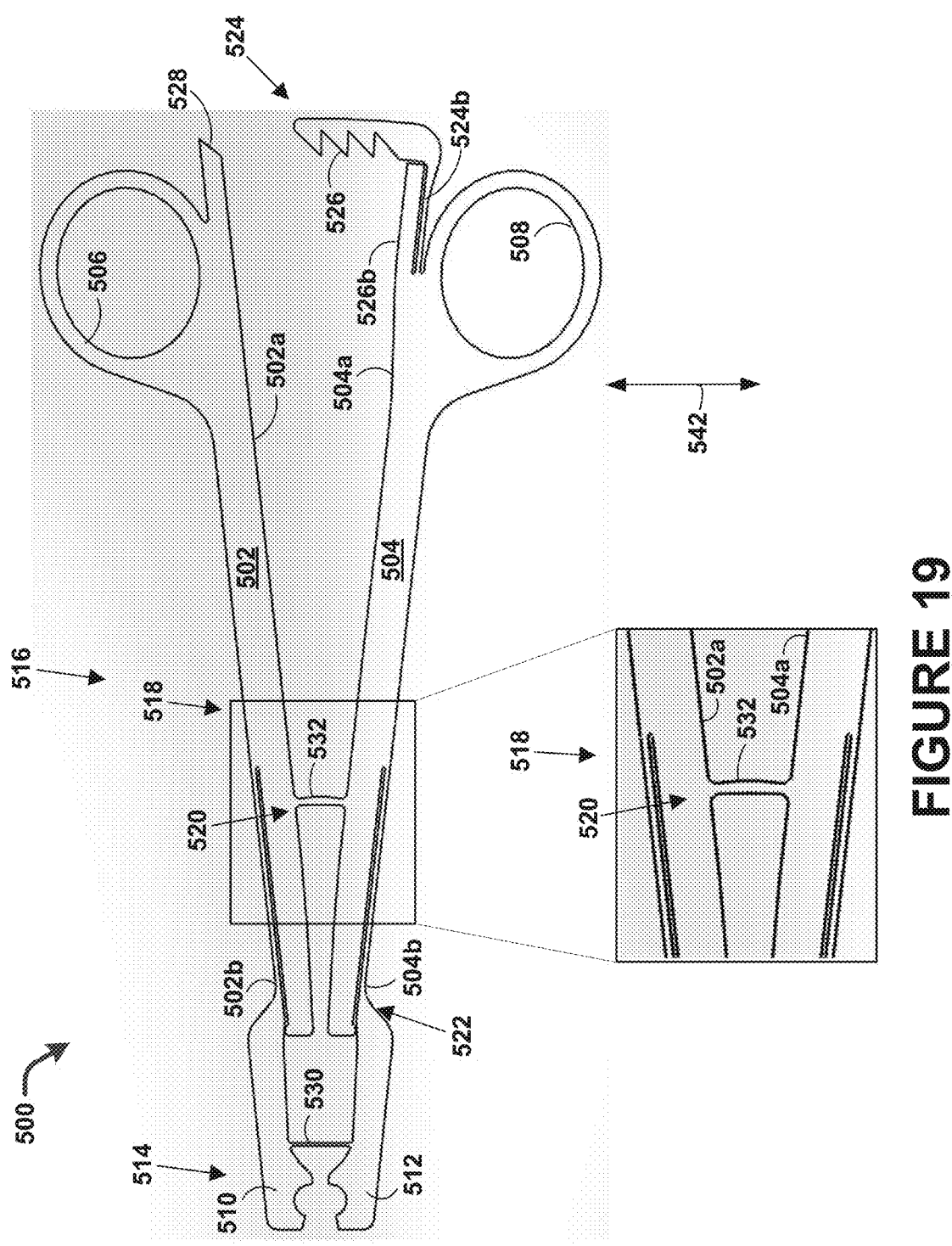
FIG. 19 is a component diagram illustrating another example implementation of a CMD surgical instrument.
Figure 20:
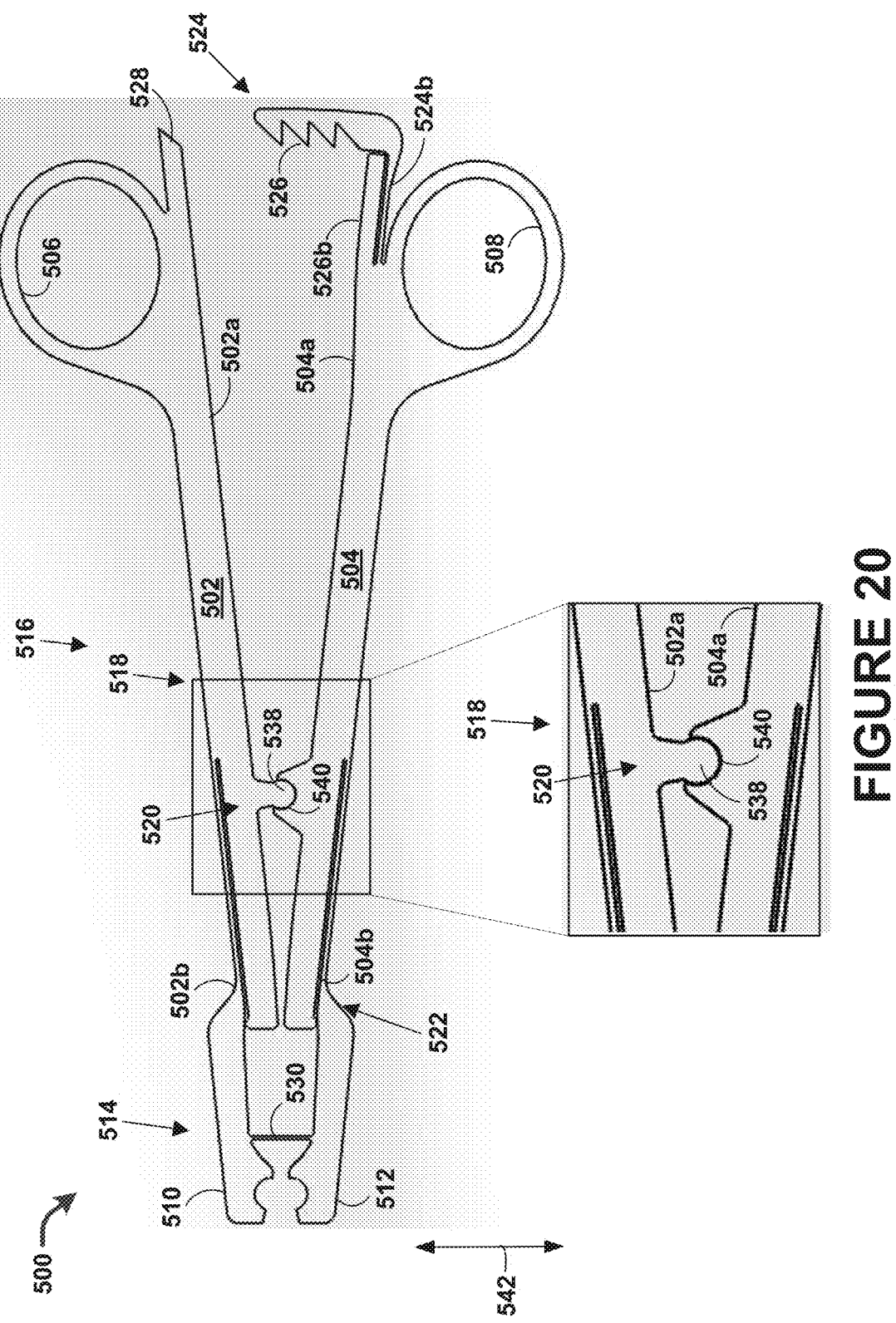
FIG. 20 is a component diagram illustrating the CMD surgical instrument of FIG. 19 incorporating a different hinge.

The CMD forceps 500 can comprise a first member 502, having a proximal end 502*a* and a distal end 502*b*, and a second member 504 having a proximal end 504*a* and a distal end 504*b*. The first and second members 502, 504 each have a finger loop 506, 508 disposed at their proximal end 502*a*, 504*a* respectively and each have a jaw 510, 512 disposed at their distal end 502*b*, 504*b* respectively. Together the jaws 510, 512 form a functional tip 514 of the surgical instrument. In this implementation, the functional tip 514 is a rod inserter, as shown in FIGS. 19 and 20.

The pair of CMD forceps 500 further comprises a midsection 516 positioned between the finger loops 506, 508 at the proximal end and the functional tip 514 at the distal end. The midsection 516 comprises a first region 518, which includes a hinge 520, and a second region 522 that is disposed proximate to the functional tip 514 and distal from the first region 518. There are multiple designs for the midsection 516 with each implementation comprising a first region 518 configured to remain elastically bendable and pivotable yet capable of carrying compression.

The finger loops 506, 508 can be any suitable size and shape for accommodating fingers. In this implementation, the finger loops 506, 508 have a circular shape.

In this implementation, the CMD forceps 500 further comprise a ratchet mechanism 524. The ratchet mechanism 524 can be included at the finger loops 506, 508 at the distal end of the CMD forceps 500. The ratchet mechanism 524 can comprise interlocking teeth that engage one another to prevent the finger loops 506, 508 of the first and second members 502, 504 from being moved away from each other. In this manner, the functional tip 514 effectively can be locked in a position, such as to clamp a rod between the jaws 510, 512. In this implementation, the ratchet mechanism 524 comprises one set of teeth 526 disposed on a surface extending from the second member 504 configured to engage a tooth 528 or teeth disposed on a surface extending from the first member 502. The thin, distal section of the ratchet mechanism 524*b* is elastic to allow for the ratcheting of the teeth. The stopper 526*b* prevents the finger loops 506 and 508 from opening up.

Figures 21, 22:
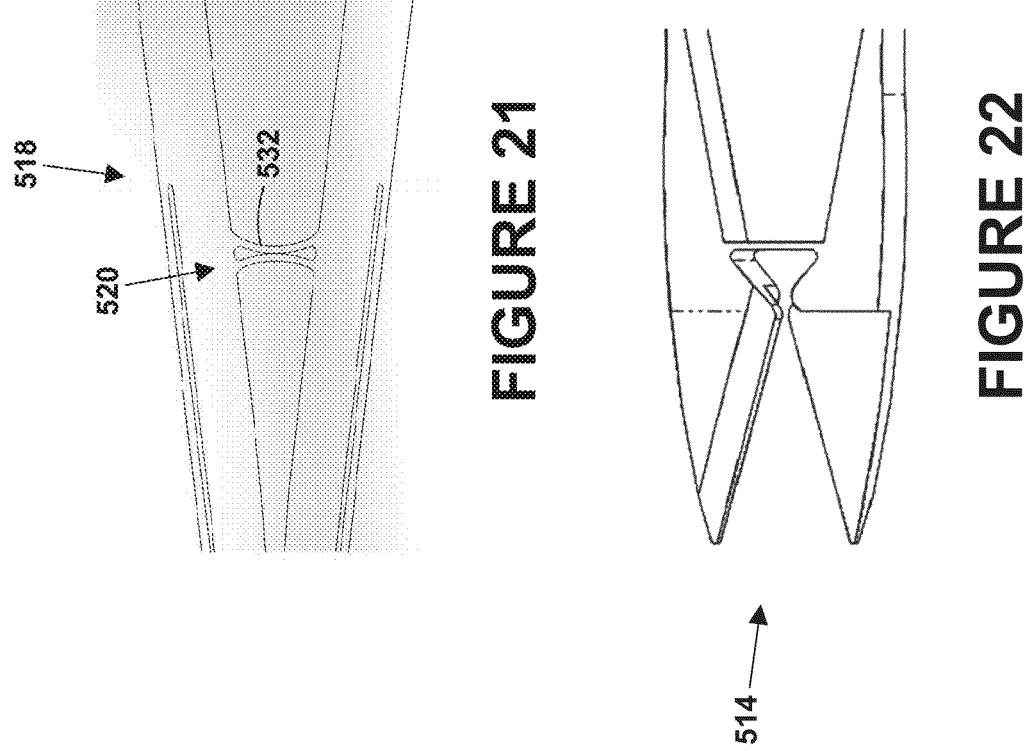
FIG. 21 is a component diagram illustrating an example implementation of a biasing member for use with the CMD surgical instrument of FIGS. 19 and 20.
FIG. 22 is a component diagram illustrating an example implementation of a functional tip for use with the CMD surgical instrument of FIGS. 19 and 20.

The jaws 510, 512 oppose one another and are configured to operatively engage each other to exert a clamping or biting force. In this example implementation, the jaws 510, 512 of the functional tip 514 comprise the forceps of a rod inserter with the medial portions of the jaws 510, 512, which face each other including surfaces configured engage a rod. As an example, the medial jaw surfaces can have a curved shape configured to grasp a cylindrical rod. The surfaces may be smooth, rough, or textured. In other implementations, the jaws 510, 512 of the functional tip 514 can comprise tweezers, regular forceps, needle nose pliers, scissors, regular pliers, compressors, and the like. In effect, the jaws 510, 512 of the functional tip 514 can comprise any current tool or instrument that comprises a single hinge mechanism. As an example, FIG. 22 shows a functional tip 514 comprising scissors with cutting surfaces disposed on the medial portions of the respective opposing jaws.

The pair of CMD forceps 500 further comprises a biasing member 530. The biasing member 530 is disposed between the first and second members 502, 504 and is integrally formed with the first and second members 502, 504. One end of the biasing member 530 is connected to the first member 502 at the functional tip 514 and the other end of the biasing member 530 is connected to the second member 504 at the functional tip 514. In effect, the first member 502 and second member 504 are interconnected via the biasing member 530 to provide integrally formed CMD forceps 500, having a monolithic body, that can be fabricated from a single sheet of metal.

Fabricating the CMD forceps 500 from a single sheet of metal can result in generally flat portions or sections. As an example, the first and second members 502, 504 can be flat on the top and bottom.

The biasing member 530 is a flexible, resilient member that is configured to apply a biasing force to the first and second members 502, 504 when the finger loops 506, 508 are closed as described in more detail below. In this example implementation, the biasing member 530 is configured to apply force to the functional tip 514 causing the jaws 510, 512 to close. The section of the functional tip 514 comprising the biasing member 530 is elastically bendable and pivotable, but carries tension.

The pair of CMD forceps 500 further comprises the hinge 520 disposed between the proximal and distal ends 502*a*, 504*a*, 502*b*, 504*b* of the first and second members 502, 504. The hinge 520 is disposed in the midsection 516 of the CMD forceps 500. In some implementations, as shown in FIG. 19, the hinge 520 can comprise a second biasing member 532 comprising a thin flexible, resilient member integrally formed with the first and second members 502, 504. The second biasing member 532 can extend between the first and second members 502, 504 and be integrally formed with the first and second members 502, 504 with one end (e.g., a first end) of the second biasing member 532 connected to and integrally formed with the first member 502 and the other end (e.g., a second end) of the second biasing member 532 connected to and integrally formed with the second member 504. As an example, the second biasing member 532 can have a first end connected to and integrally formed with the first member 502 and a second end connected to and integrally formed with the second member 504*a* with the second biasing member 532 extending between the first member 502 and the second member 504 to form a first hinge point and render the hinge 520 pivotable. In other implementations, as shown in FIG. 21, the hinge 520 can comprise a second biasing member 532 comprising a pair of thin flexible, resilient members that are each integrally formed with the first and second members. The pair of resilient members are disposed next to each other and separated by a gap. The resilient members can be curved, in particular when force is applied to the CMD forceps 500 by squeezing the finger loops 506, 508 together which causes flexing/bending of the resilient members. The midsection 516 comprising the hinge 520 is configured to remain elastically bendable and pivotable yet capable of carrying compression.

In other implementations, as shown in FIG. 20, the hinge 520 is disposed in the midsection 516 of the CMD forceps 500 and can comprise a first portion on the first member 502, such as a boss 538, that is configured to mate with a complementary second portion on the second member 504, such as a socket 540 adapted to receive the boss 538, to form the hinge 520 or pivot. The mated first and second portions form a first hinge point and are configured to mechanically interact to render the hinge 520 pivotable. In some non-limiting examples, the boss 538 can comprise a circular head that is configured to be selectably inserted into a complementary circular opening of the socket 540. Mating the boss 538 with the complementary socket 540 renders the hinge 520 functional or pivotable. In FIG. 20, the first member 502 comprises the boss 538 and the second member 504 comprises the socket 540. But, it should be understood from this disclosure that in other implementations the second member can comprise the boss and the first member can comprise the complementary socket of the hinge or pivot.

FIG. 19 illustrates the CMD forceps 500 in an operational configuration in which the CMD forceps 500 are in a functional ready-to-use state for performing surgical procedures. FIG. 19 also illustrates at the same time, the cleaning configuration. No tangential surfaces or small cavities, which could cause capillary action, are present.

The CMD forceps 500, as shown in FIG. 20, can transition from a non-operational configuration or cleaning configuration, not shown, to an operational configuration, as shown in FIG. 20. The boss 538 is configured to be mated with the complementary socket 540 by manually lifting, along vertical axis 542, the boss-containing part of the first member 502 out of planar alignment with the second member 504. The boss-containing part of the first member 502 is moved in the direction of the complementary socket 540 of the second member 504 until the boss 538 is aligned directly over (or under) the complementary socket 540. Finally, the boss 538 is moved linearly by lowering (or lifting) the boss 538 into the socket 540 to selectably insert the boss 538 into the complementary socket 540. This reestablishes the substantially coplanar alignment of the first member 502 and second member 504 and forms the hinge 520 or pivot.

Thus, to summarize, the CMD forceps 500 can transition from the non-operational configuration, or cleaning configuration, to the operational configuration by inserting the boss 538 into the complementary socket 540 to mate the boss 538 with the complementary socket 540. Mating the boss 538 with the complementary socket 540 forms the hinge 520. And, once mated, the first member 502 and the second member 504 are substantially coplanar.

The practical operation of the CMD forceps 500 begins with actuating the CMD forceps 500 by forcing the first and second members 502, 504 towards each other, such as by manually squeezing together (e.g., pushing towards each other) the finger loops 506, 508. The finger loops 506, 508 are biased away from each other by the second biasing member 532 of the hinge 520 that is disposed in the space between the first and second members 502, 504. Forcing the finger loops 506, 508 towards each other causes the first region 518 of the midsection 516 to act as a pivot point under compression at the hinge 520. The pivoting at the hinge 520 of the first region 518 causes the second region 522 of the midsection 516 to open. This in turn causes the section of the functional tip 514 containing the resilient biasing member 530 to act as a pivot point under tension which causes the jaws 510, 512 of the functional tip 514 to close. All of these movements are elastic and do not result in permanent deformations.

It will be appreciated from this disclosure that the CMD forceps 500 does not contain tangential surface contacts and does not include cavities of a size that facilitates capillary action. Thus, the CMD forceps 500 of this disclosure has cavities that, if present, are sufficiently large to avoid capillary action. As a result, the CMD forceps 500 can be completely cleaned and sterilized.

The CMD forceps 500 can transition from the operational configuration, as shown in FIG. 20, to the non-operational configuration or cleaning configuration by disengaging the hinge 520 to facilitate cleaning and sterilization of the CMD forceps 500. The hinge 520 can be disengaged by removing the boss 538 from the socket 540 by manually lifting the boss 538 linearly, or vertically along axis 542, from the socket 540 such that the first member 502 is not in planar alignment with the second member 504 (i.e., the first and second members 502, 504 are not coplanar). The boss-containing part of the first member 502 can then be moved in a direction away from the complementary socket 540 of the second member 504 after which the first member 502 and second member 504 can be placed into substantially coplanar alignment. This places the CMD forceps 500 in the non-operational configuration or cleaning configuration.

Figure 23:
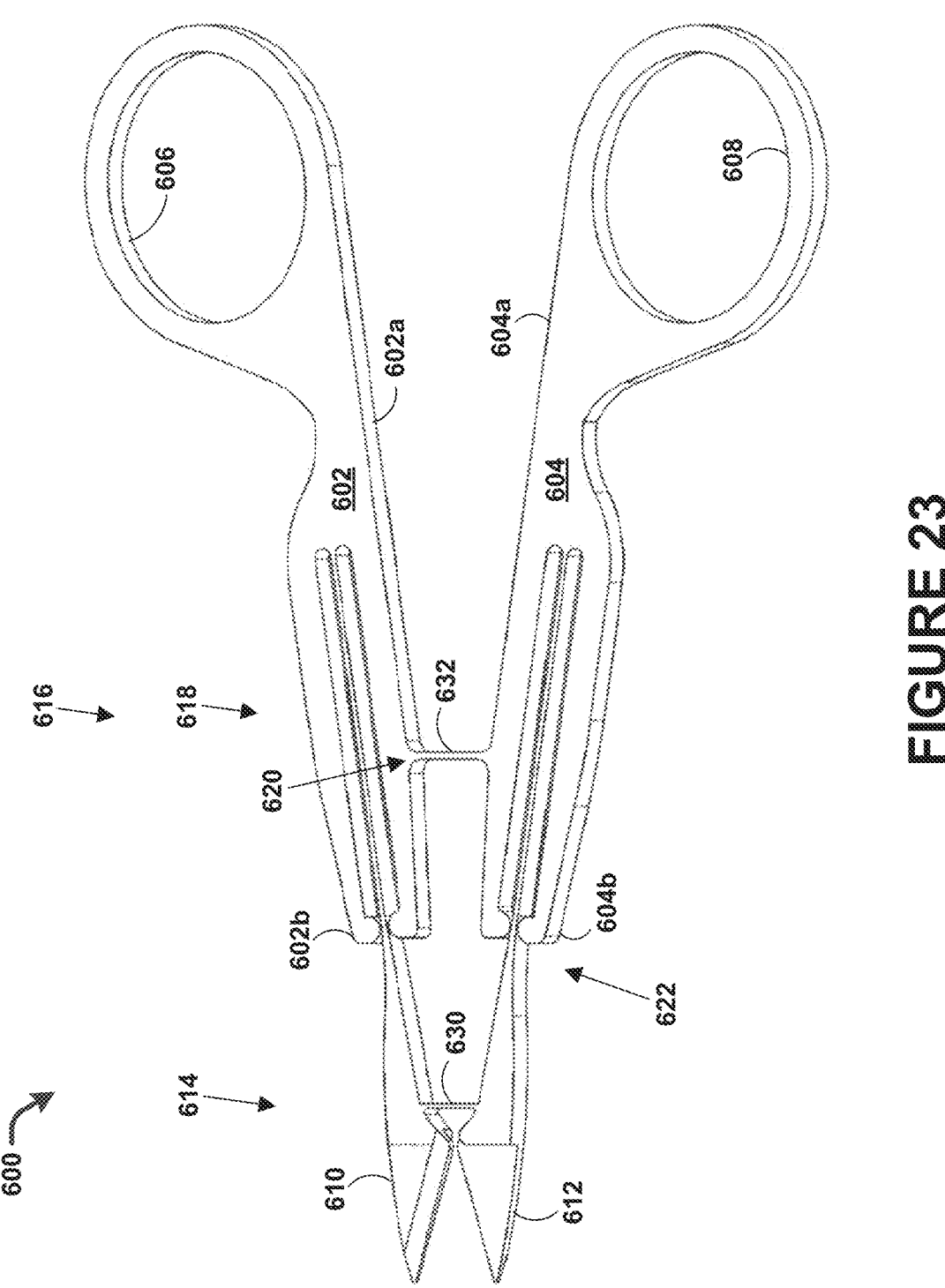
FIG. 23 is a component diagram of yet another example implementation of a CMD surgical instrument in accordance with this disclosure.

Referring now to FIG. 23, there is illustrated another example implementation of a CMD surgical instrument. In this example implementation, the CMD surgical instrument is a pair of CMD scissors 600. The CMD scissors 600 can be formed from a single piece or sheet of metal or elastomeric polymer.

The CMD scissors 600 can comprise a first member 602, having a proximal end 602a and a distal end 602b, and a second member 604 having a proximal end 604a and a distal end 604b. The first and second members 602, 604 each have a finger loop 606, 608 disposed at their proximal end 602a, 604a respectively and each have a jaw 610, 612 disposed at their distal end 602b, 604b respectively. The jaws 610, 612 of the first and second members 602, 604 oppose one another and together form a functional tip 614 of the surgical instrument. In this implementation, the functional tip 614 is scissors.

The pair of CMD scissors 600 further comprises a midsection 616 positioned between the finger loops 606, 608 at the proximal end and the functional tip 614 at the distal end. The midsection 616 comprises a first region 618, which includes a hinge 620, and a second region 622 that is disposed proximate to the functional tip 614 and distal from the first region 618. There are multiple designs for the midsection 616 with each implementation comprising a first region 618 configured to remain elastically bendable and pivotable yet capable of carrying compression.

The finger loops 606, 608 can be any suitable size and shape for accommodating fingers. In this implementation, the finger loops 606, 608 have a circular shape.

The jaws 610, 612 oppose one another and are configured to operatively engage each other to exert a clamping or biting force. In this example implementation, the jaws 610, 612 of the functional tip 614 comprise scissors with the medial portions of the jaws 610, 612, which face each other, including sharp cutting surfaces. As an example, the medial jaw surfaces can have be angled so as to form blades for cutting.

The pair of CMD scissors 600 further comprises a biasing member 630. The biasing member 630 is disposed between the first and second members 602, 604 and is integrally formed with the first and second members 602, 604. One end of the biasing member 630 is connected to the first member 602 at the functional tip 614 and the other end of the biasing member 630 is connected to the second member 604 at the functional tip 614. In effect, the first member 602 and second member 604 are interconnected via the biasing member 630 to provide integrally formed CMD scissors 600, having a monolithic body, that can be fabricated from a single sheet of metal.

Fabricating the CMD scissors 600 from a single sheet of metal can result in generally flat portions or sections. As an example, the first and second members 602, 604 can be flat on the top and bottom.

The biasing member 630 is a flexible, resilient member that is configured to apply a biasing force to the first and second members 602, 604 when the finger loops 606, 608 are closed as described in more detail below. In this example implementation, the biasing member 630 is configured to apply force to the functional tip 614 causing the jaws 610, 612 to close. The section of the functional tip 614 comprising the biasing member 630 is elastically bendable and pivotable, but carries tension.

The pair of CMD scissors 600 further comprises the hinge 620 disposed between the proximal and distal ends 602*a*, 604*a*, 602*b*, 604*b* of the first and second members 602, 604. The hinge 620 is disposed in the midsection 616 of the CMD scissors 600. In this implementation, the hinge 620 comprises a second biasing member 632 comprising a thin flexible, resilient member integrally formed with the first and second members 602, 604. In other implementations, the hinge 620 can comprise a pair of thin flexible, resilient members or a boss-socket configuration.

FIG. 23 illustrates the CMD scissors 600 in an operating configuration in which the CMD scissors 600 are in a functional ready-to-use state for performing surgical procedures.

The practical operation of the CMD scissors 600 beings with actuating the CMD scissors 600 by manually squeezing together (e.g., pushing towards each other) the finger loops 606, 608. The finger loops 606, 608 are biased away from each other by the second biasing member 632 of the hinge 620 that is disposed in the space between the first and second members 602, 604. Forcing the finger loops 606, 608 towards each other causes the first region 618 of the midsection 616 to act as a pivot point under compression at the hinge 620. The pivoting at the hinge 620 of the first region 618 causes the second region 622 of the midsection 616 to open. This in turn causes the section of the functional tip 614 containing the resilient biasing member 630 to act as a pivot point under tension which causes the jaws 610, 612 of the functional tip 614 to close. All of these movements are elastic and do not result in permanent deformations.

It will be appreciated from this disclosure that the CMD scissors 600 does not contain tangential surface contacts and does not include cavities of a size that facilitates capillary action. Thus, the CMD scissors of this disclosure has cavities that, if present, are sufficiently large to avoid capillary action. As a result, the CMD scissors can be completely cleaned and sterilized. To facilitate cleaning and sterilization of the CMD scissors, the hinge can be disengaged, if applicable.

Figures 24, 25:
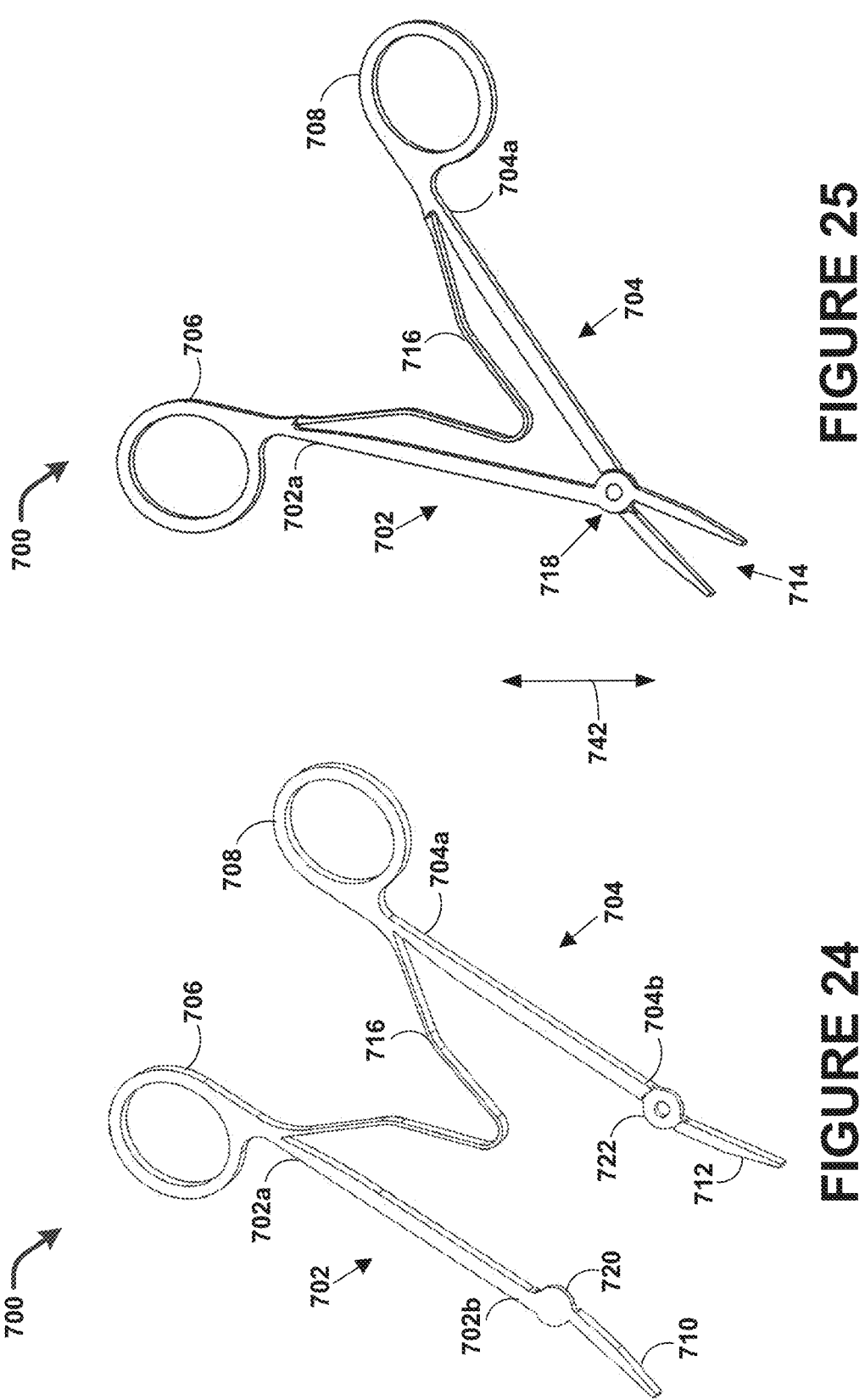
FIG. 24 is a component diagram of yet another example implementation of a CMD surgical instrument in accordance with this disclosure in a cleaning configuration.
FIG. 25 is a component diagram of the CMD surgical instrument of FIG. 24 in a ready-to-use or operating configuration.

Referring now to FIGS. 24-25, there is illustrated another example implementation of a CMD surgical instrument. In this example implementation, the CMD surgical instrument is a pair of CMD forceps 700. The CMD forceps can be formed from a single piece of metal material or elastomeric polymer. In some implementations, the CMD forceps are cut from a single piece of metal, such as a metal sheet.

The CMD forceps 700 can comprise a first member 702, having a proximal end 702*a* and a distal end 702*b*, and a second member 704 having a proximal end 704*a* and a distal end 704*b*. The first and second members 702, 704 each have a finger loop 706, 708 disposed at their proximal end 702*a*, 704*a* respectively and each have a jaw 710, 712 disposed at their distal end 702*b*, 704*b* respectively. Together the jaws 710, 712 form a functional tip 714 of the surgical instrument. In this implementation, the functional tip 714 is forceps. Although not shown, in some implementations the CMD forceps 700 can comprise a ratchet mechanism that is included at the finger loops 706, 708 similar to that shown in FIGS. 19 and 20.

The jaws 710, 712 oppose one another and are configured to operatively engage each other to exert a clamping or biting force. In this implementation, the jaws 710, 712 of the functional tip 714 comprise forceps with medial portions of the jaws 710, 712 that face each other having smooth engagement surfaces or interlocking teeth. In other implementations, the jaws 710, 712 of the functional tip 714 comprise scissors with the medial portions of the jaws that face each other including sharpened surfaces to form cutting blades. In other implementations, the jaws 710, 712 of the functional tip 714 can comprise tweezers, a rod inserter, needle nose pliers, regular pliers, compressors, and the like. In effect, the jaws 710, 712 of the functional tip 714 can comprise any current tool or instrument that comprises a single hinge mechanism.

The CMD forceps 700 further comprise a biasing member 716. The biasing member 716 is disposed between the first and second members 702, 704 and is integrally formed with the first and second members 702, 704 with one end of the biasing member 716 connected to the first member 702 at the proximal end 702*a*, such as at or near the finger loop 706, and the other end of the biasing member 716 connected to the second member 704 at the proximal end 704*a*, such as at or near the finger loop 708. As an example, the biasing member 716 can have a first end and a second end and the biasing member 7166 can extend between the first member 702 and the second member 704 with the first end connected to and integrally formed with the first member 702 and the second end connected to and integrally formed with the second member 704. In effect, the first member 702 and second member 704 are interconnected via the biasing member 716 to provide integrally formed CMD forceps 700, having a monolithic body, that can be fabricated from a single sheet of metal. Fabricating the CMD forceps 700 from a single sheet of metal can result in generally flat portions or sections. As an example, the first and second members 702, 704 can be flat on the top and bottom.

The biasing member 716 is a flexible, resilient member that is configured to apply a biasing force to the first and second members 702, 704 when the finger loops 706, 708 are closed as described in more detail below. The biasing member 716 can be curved.

Disposed between the proximal and distal ends 702*a*, 704*a*, 702*b*, 704*b* of the first and second members 702, 704 is a hinge 718. The hinge 718 is disposed proximate to the jaws 710, 712 and distal to the finger loops 706, 708 of the CMD forceps 700. The hinge 718 can comprise a first portion, such as an engaging protrusion 720, that is configured to mate with a complementary second portion, such as a complementary receiving slot 722 adapted to receive the engaging protrusion 720, to form the hinge 718 or pivot. Mating the first and second portions such as, for example, the engaging protrusion 720 with the complementary receiving slot 722, forms a first hinge point and renders the hinge 718 functional or pivotable. In this implementation, the first member 702 comprises the engaging protrusion 720 and the second member 704 comprises the receiving slot 722. But, it should be understood from this disclosure that in other implementations the second member 704 can comprise the engaging protrusion and the first member 702 can comprise the complementary receiving slot of the hinge or pivot.

FIG. 24 shows the CMD forceps 700 after manufacturing with the CMD forceps 700 disposed in a non-operational configuration or cleaning configuration, which allows for complete cleaning and sterilization of the surgical instrument. FIG. 25 shows the CMD forceps 700 in an operational configuration, which renders the CMD forceps 700 functional and ready-to-use for performing surgical procedures.

FIGS. 24-25 illustrate that the CMD forceps 700 can transition from the non-operational configuration or cleaning configuration, as shown in FIG. 24, to an operational configuration for surgical use, as shown in FIG. 25, by manually lifting, along vertical axis 742, the engaging protrusion-containing part of the first member 702 out of planar alignment with the second member 704. The engaging protrusion-containing part of the first member 702 is moved in the direction of the complementary receiving slot 722 of the second member 704 until the engaging protrusion 720 is aligned directly over or under the complementary receiving slot 722. Finally, the engaging protrusion 720 is moved linearly by lowering the engaging protrusion 720 into the receiving slot 722 to selectably insert the engaging protrusion 720 into the complementary receiving slot 722. This reestablishes the substantially coplanar alignment of the first member 702 and second member 704 and forms the hinge 718 or pivot. Once the engaging protrusion 720 is selectably inserted into the receiving slot 722 the CMD surgical instrument performs like any normal compressor, scissors, or pliers depending on the type of functional tip.

Thus, to summarize, the CMD forceps 700 can transition from the non-operational configuration or cleaning configuration, as shown in FIG. 24, to the operational configuration by inserting the engaging protrusion 720 into the complementary receiving slot 722 to mate the engaging protrusion 720 with the receiving slot 722. Mating the engaging protrusion 720 with the complementary receiving slot 722 forms the hinge 718. And, once mated, the first member 702 and the second member 704 are substantially coplanar.

The practical operation of the CMD forceps 700 beings with actuating the CMD forceps 700 by forcing the first and second members 702, 704 towards each other, such as by manually closing (e.g., squeezing together) the finger loops 706, 708. The finger loops 706, 708 are biased away from each other by the biasing member 716 disposed in the space between the first and second members 702, 704. Forcing the finger loops 706, 708 towards each other causes the biasing member 716 to exert an increased biasing force which causes pivoting at the hinge 718. This pivoting at the hinge 718 triggers the opposing jaws 710, 712 to move towards one another in a biting fashion causing the functional tip 714 to close.

The CMD forceps 700 can transition from the operational configuration to the non-operational configuration, or cleaning configuration, by disengaging the hinge 718. The hinge 718 can be disengaged by removing the engaging protrusion 720 from the receiving slot 722 by manually lifting the engaging protrusion 720 linearly, or vertically along axis 742, from the receiving slot 722 such that the first member 702 is not in planar alignment with the second member 704 (i.e., the first and second members 702, 704 are not coplanar). The engaging protrusion-containing part of the first member 702 can then be moved in a direction away from the complementary receiving slot 722 of the second member 704 after which the first member 702 and second member 704 can be placed into substantially coplanar alignment.

This places the CMD forceps 700 in the non-operational configuration. Disposing the CMD forceps 700 in the non-operational configuration allows for the complete cleaning and sterilization of the CMD surgical instrument because there are no tangential surface contacts and any cavities that are present on the CMD forceps 700 are sufficiently large to avoid capillary action.

Figures 26, 27:
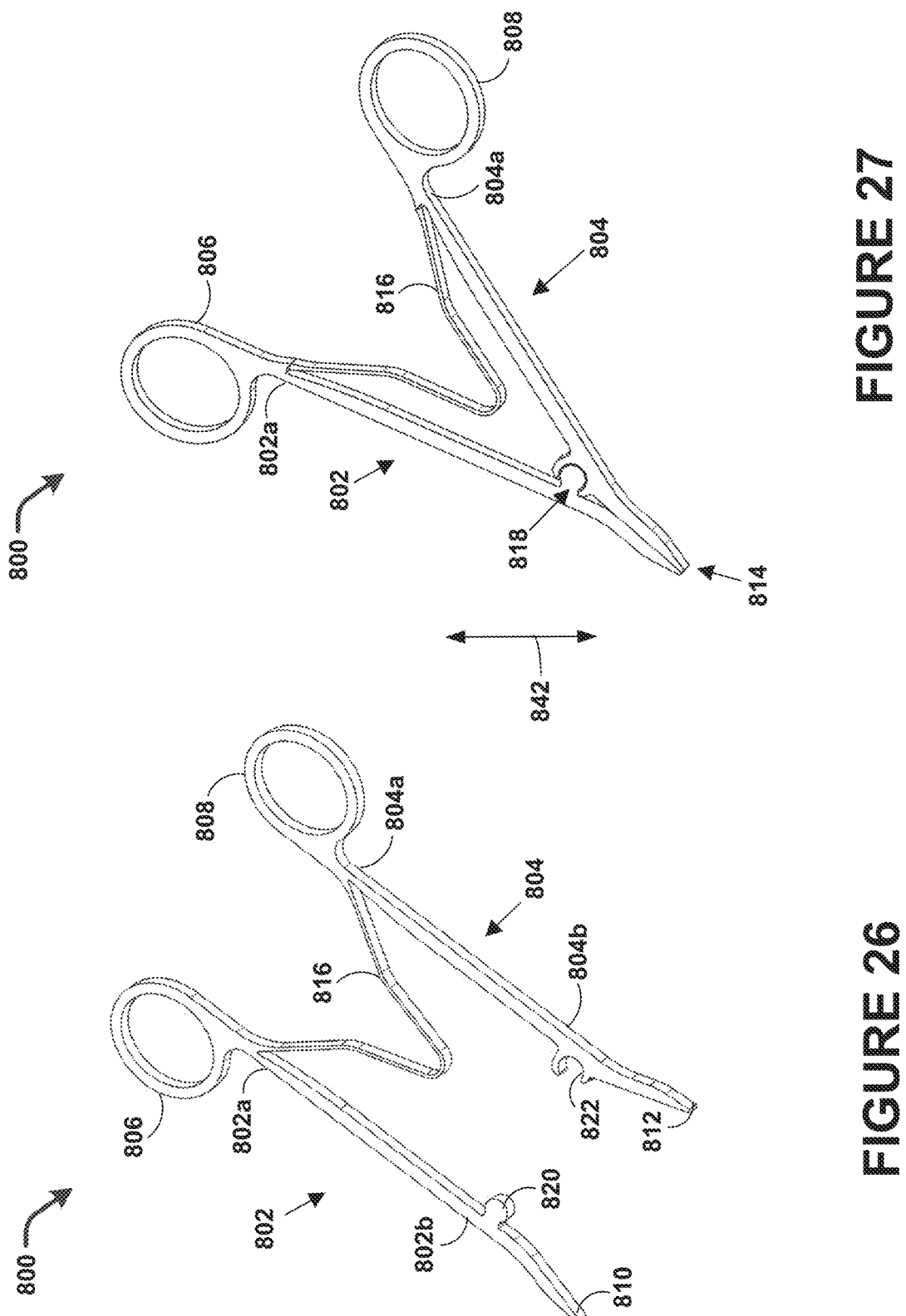
FIG. 26 is a component diagram of another example implementation of a CMD surgical instrument in accordance with this disclosure in a cleaning configuration.
FIG. 27 is a component diagram of the CMD surgical instrument of FIG. 26 in a ready-to-use or operating configuration.
Figures 28A, 28B:
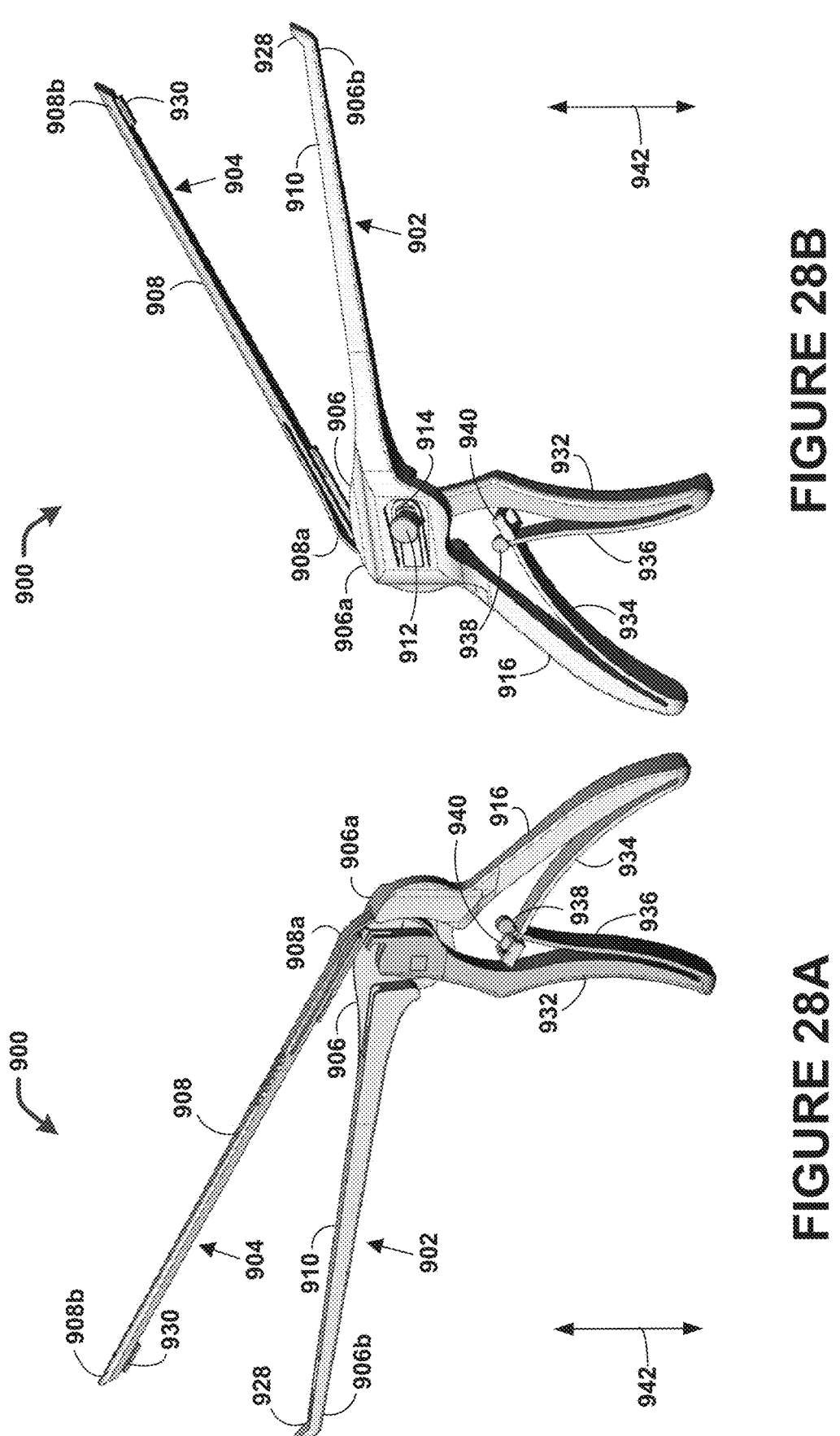
FIGS. 28A and 28B are component diagrams illustrating another example implementation of a CMD surgical instrument in accordance with this disclosure.
Figure 29:
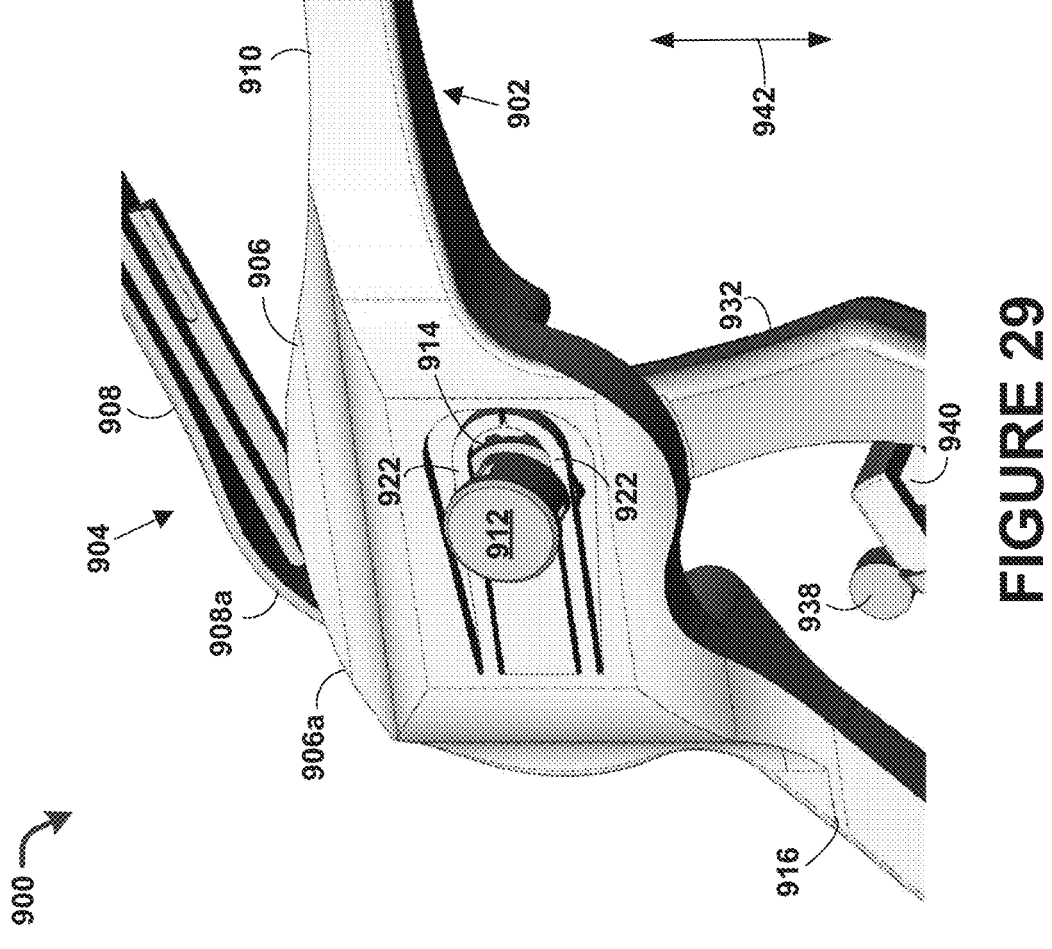
FIG. 29 is a component diagram illustrating one or more portions of the CMD surgical instrument of FIGS. 28A and 28B.
Figures 30, 31:
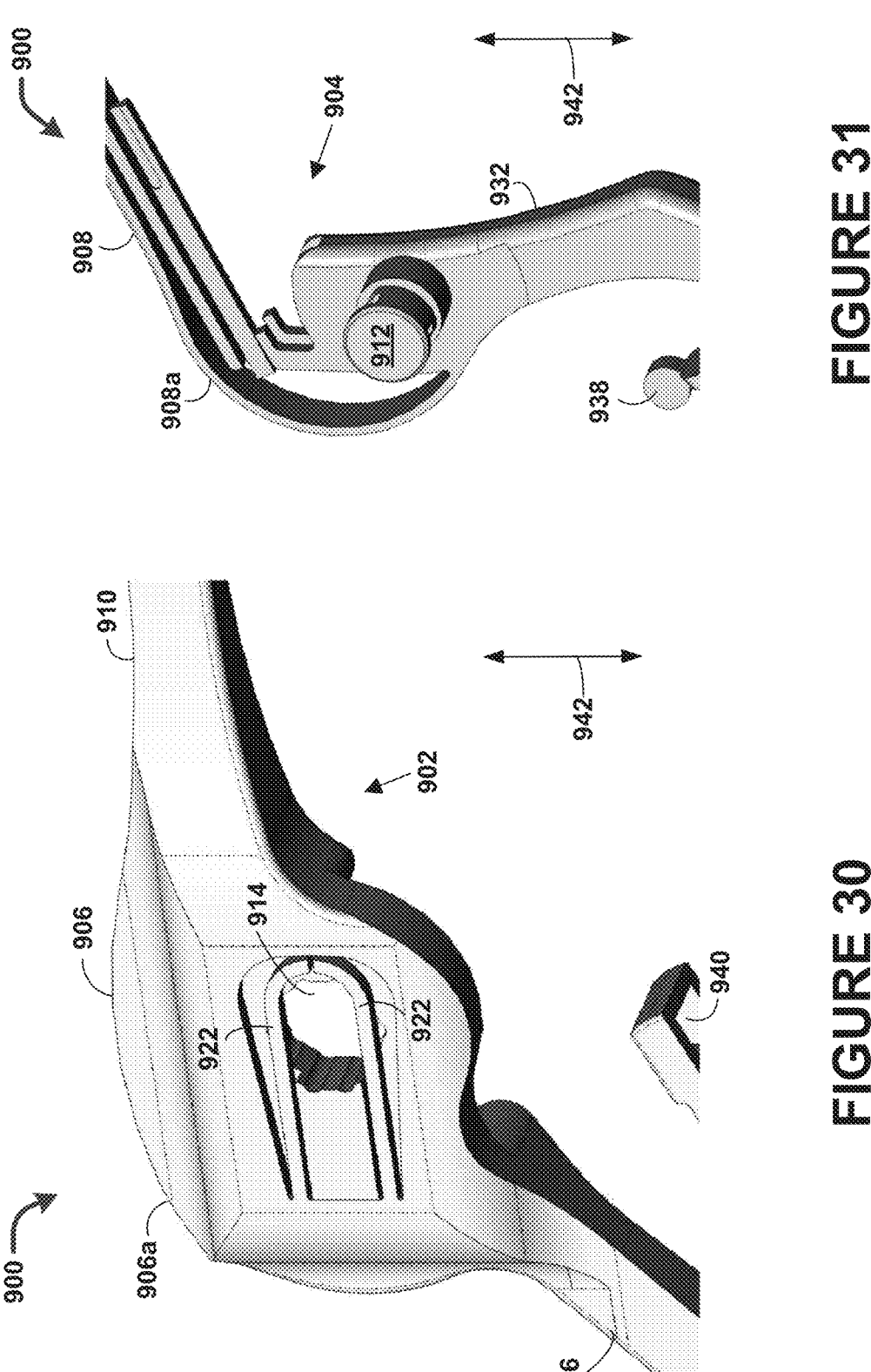
FIG. 30 is a component diagram illustrating one or more portions of the CMD surgical instrument of FIGS. 28A and 28B.
FIG. 31 is a component diagram illustrating one or more portions of the CMD surgical instrument of FIGS. 28A and 28B.

Referring now to FIGS. 26-27, there is illustrated another example implementation of a CMD surgical instrument. In this example implementation, the CMD surgical instrument is a CMD spreader 800, also referred to as a CMD distractor. The CMD spreader 800 can be formed from a single piece of metal material or elastomeric polymer. In some implementations, the CMD spreader 800 is cut from a single piece of metal, such as a metal sheet. The CMD spreader 800 has many features in common with the CMD forceps 700 illustrated in FIGS. 24-25. For the sake of brevity, those features that are structurally and functionally similar will not be described below.

The jaws 810, 812 oppose one another and are configured to cooperatively disengage each other to exert a force, such as a spreading force. In this implementation, the jaws 810, 812 of the functional tip 814 comprises a spreader with medial portions of the jaws 810, 812, which face each other, including surfaces configured for engagement.

Disposed between the proximal and distal ends 802*a*, 804*a*, 802*b*, 804*b* of the first and second members 802, 804 is a hinge 818. The hinge 818 is disposed proximate to the jaws 810, 812 and distal to the finger loops 806, 808 of the CMD spreader 800. The hinge 818 can comprise a first portion on the first member 802, such as a boss 820, that is configured to mate with a second portion on the second member 804, such as a complementary socket 822 adapted to receive the boss 820, to form the hinge 818 or pivot. The mated first and second portions form a first hinge point and are configured to mechanically interact to render the hinge 818 pivotable. Mating the boss 820 with the complementary socket 822 renders functional the hinge 818 or pivot. In this implementation, the first member 802 comprises the boss 820 and the second member 804 comprises the socket 822. But, it should be understood from this disclosure that in other implementations the second member 804 can comprise the boss and the first member 802 can comprise the complementary socket of the hinge or pivot.

FIG. 26 shows the CMD spreader 800 after manufacturing with the CMD spreader 8100 disposed in a non-operational configuration or cleaning configuration, which allows for complete cleaning and sterilization of the surgical instrument. FIG. 27 shows the CMD spreader 800 in an operational configuration, which renders the CMD spreader 800 functional and ready-to-use for performing surgical procedures.

FIGS. 26-27 illustrate that the CMD spreader 800 can transition from the non-operational configuration or cleaning configuration, as shown in FIG. 26, to an operational configuration or operating configuration, as shown in FIG. 27, by manually lifting, along vertical axis 842, the boss-containing part of the first member 802 out of planar alignment with the second member 804. The boss-containing part of the first member 802 is moved in the direction of the complementary socket 822 of the second member 804 until the boss 820 is aligned directly over or under the complementary socket 822. Finally, the boss 820 is moved linearly by lowering the boss 820 into the socket 822 to selectably insert the boss 820 into the complementary socket 822. This reestablishes the substantially coplanar alignment of the first member 802 and second member 804 and forms the hinge 818 or pivot. Once the boss is selectably inserted into the socket the CMD surgical instruments performs like any normal compressor, scissors, or pliers depending on the type of functional tip.

The practical operation of the CMD spreader 800 beings with actuating the CMD spreader 800 by manually closing (e.g., squeezing together) the finger loops 806, 808. The finger loops 806, 808 are biased away from each other by the biasing member 816 disposed in the space between the first and second members 802, 802. Forcing the finger loops 806, 808 towards each other causes the biasing member 816 to exert an increased biasing force which causes pivoting at the hinge 818. This pivoting at the hinge 818 triggers the opposing jaws 810, 812 to move away from one another resulting in the opening of the functional tip 814. Thus, closing the finger loops 806, 808 together causes the jaws 810, 812 to move away from each other and the functional tip 814 to open (and not close like a pair of scissors).

The CMD spreader 800 can transition from the operational configuration, or operating configuration, to the non-operational configuration, or cleaning configuration, by disengaging the hinge 818. The hinge 818 can be disengaged by removing the boss 820 from the socket 822 in a manner similar to that described above with respect to FIG. 20. This places the CMD spreader 800 in the non-operational configuration. Disposing the CMD spreader 800 in the non-operational configuration allows for the complete cleaning and sterilization of the CMD surgical instrument because there are no tangential surface contacts and any cavities that are present on the CMD spreader are sufficiently large to avoid capillary action.

Referring now to FIGS. 28A through 35, there is illustrated another example implementation of a CMD surgical instrument. In this implementation, the CMD surgical instrument comprises a CMD kerrison-rongeur 900. The CMD kerrison-rongeur 900 can be formed from two pieces of metal or elastomeric polymer. The CMD kerrison-rongeur 900 is an alternative implementation of the CMD kerrison-rongeur 200 discussed above with respect to FIGS. 4-10B and 11B. The two implementations have many features in common. For the sake of brevity, the primary focus of the following paragraphs will be directed to the structural differences of the CMD kerrison-rongeur 900 with respect to the CMD kerrison-rongeur 200.

In this implementation, the CMD kerrison-rongeur 900 can comprise a first member 902 and a separate second member 904 with the first and second members 902, 904 configured to be removably coupled. The first member 902 generally comprises an elongated track member 906 having a proximal end 906a and a distal end 906b. The second member 904 generally comprises an elongated cutting slide 908 have a proximal end 908a and a distal end 908b. The elongated track member 906 can comprise a track 910 that extends longitudinally along a length of the elongated track member 906.

Figure 33:
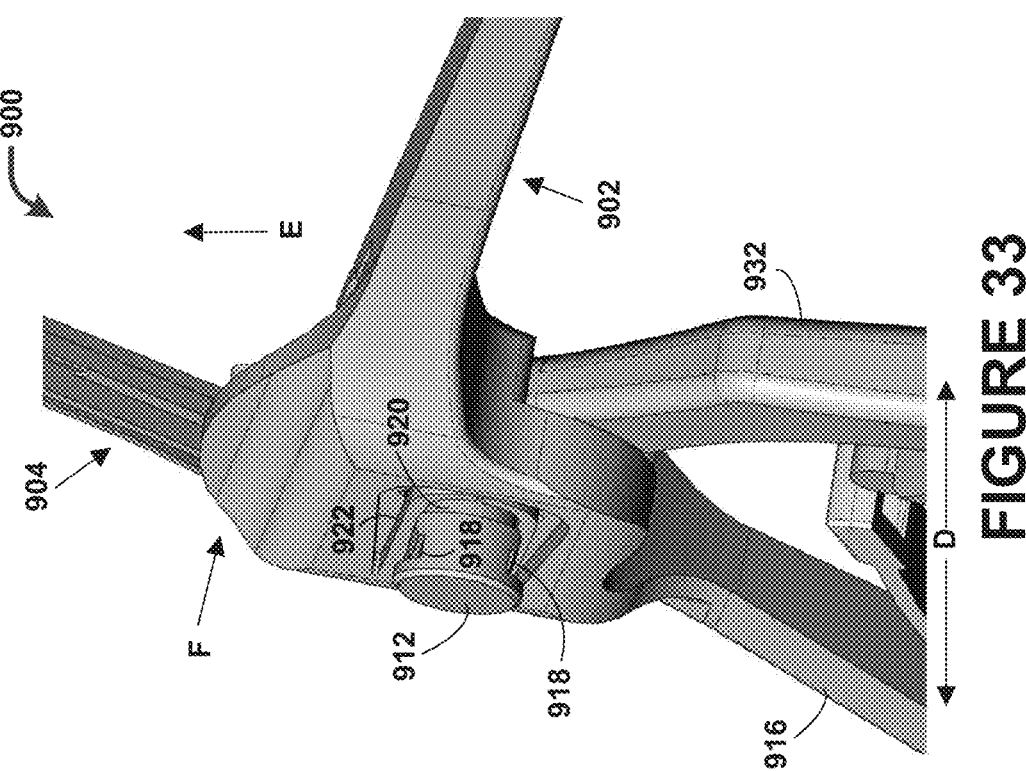
FIG. 33 is a component diagram illustrating one or more portions of the CMD surgical instrument of FIGS. 28A and 28B during disassembly as the instrument transitions from the operational configuration to a non-operational configuration.
Figure 32:
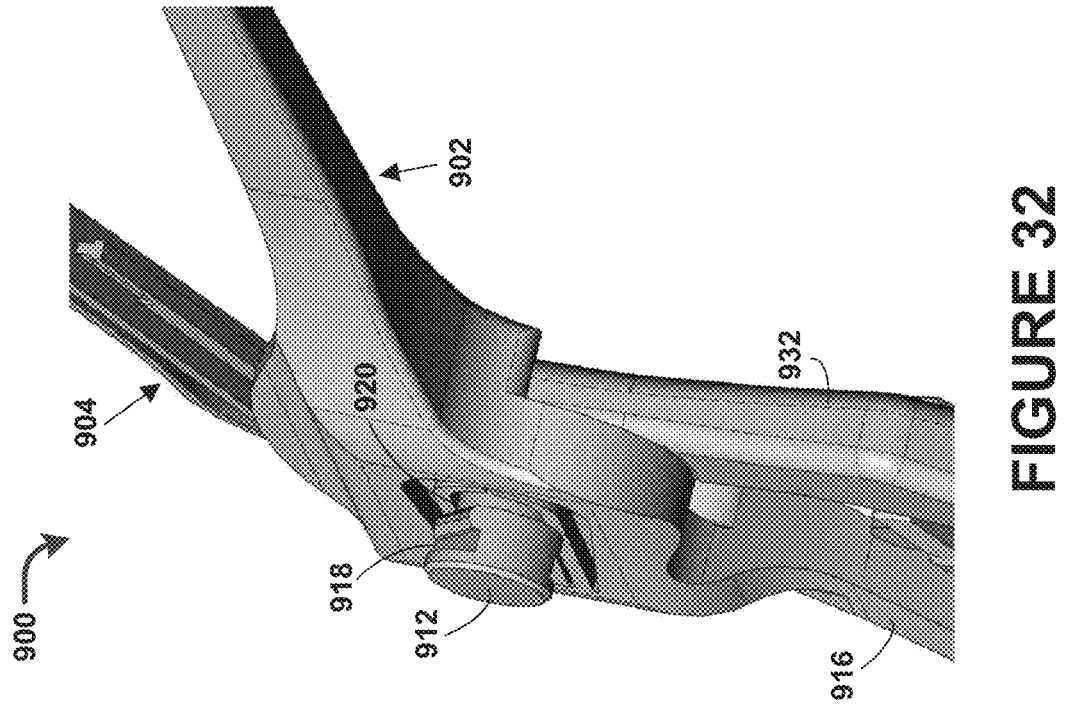
FIG. 32 is a component diagram illustrating one or more portions of the CMD surgical instrument of FIGS. 28A and 28B in in a surgical use or operational configuration.
Figures 34, 35:
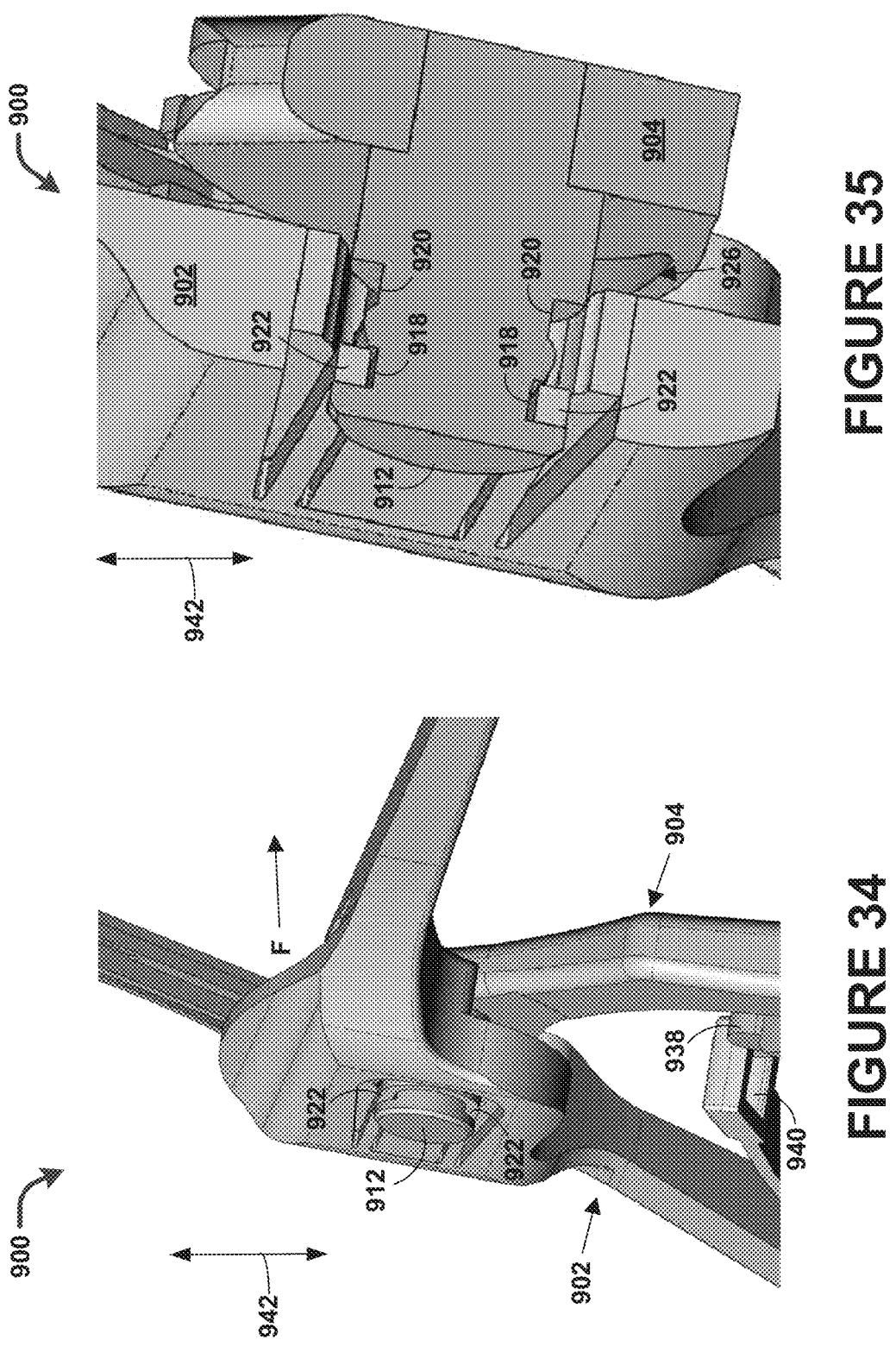
FIG. 34 is a component diagram illustrating one or more portions of the CMD surgical instrument of FIGS. 28A and 28B during disassembly as the instrument transitions from the operational configuration to a non-operational configuration.
FIG. 35 is a component diagram illustrating the CMD surgical instrument of FIGS. 28A and 28B in the non-operational configuration or cleaning configuration.

The second member 904 further comprises a boss 912 that is configured to be mated with a hole 914 disposed in the first member 902 by slidably inserting the boss 912 into the hole 914. The boss 912 can be disposed adjacent the proximal end 908a of the elongated cutting slide 908 where the elongated cutting slide 908 terminates in a handle 932 as described in detail below. The boss 912 protrudes from the surface of the second member 904 and can include two or more grooves, such as a first groove 918 and a second groove 920, as shown in FIGS. 32, 33, and 35. Each groove 918, 920 may be continuous and extend around the entire perimeter of the boss 912 or discontinuous in which the groove 918, 920 does not extend around the entire perimeter of the boss 912.

In some implementations, the boss 912 includes two grooves 918, 920. The first groove 918 can be discontinuous such that the first groove 918 does not extend around the entire perimeter of the boss 912, as shown in FIGS. 32, 33, and 35. Instead, the first groove 918 can comprise a pair of grooves with each groove disposed on opposite sides of the boss 912 and arranged in coplanar alignment. The second groove 920 can be continuous and extend around the entire perimeter of the boss 912, but is not required to. The first groove 918 may allow and, in some instances may even help guide, the first member 902 to slide along an axis of the boss 912 when the boss 912 is disposed in the hole 914 (e.g., after mating the first and second members 902, 904) as described below. The boss 912 can be any suitable size and shape that permits the boss 912 to be slidably inserted into, and mated with, the complementary hole 914 of the first member 902. In some implementations, the boss 912 comprises a circular-shaped protrusion that is configured to be mated with the hole 914 having a size and shape adapted to receive the boss 912 therein.

The first member 902 can comprise one or more retaining members 922 disposed adjacent the hole 914, as shown in FIGS. 29 through 33. In some implementations, the one or more retaining members 922 can be disposed around the hole 914 and help define the hole 914. The one or more retaining members 922 can be configured to selectably engage the corresponding grooves 918, 920 of the boss 912 with the retaining member 922 disposed in a corresponding groove 918, 920 in order to removably couple the second member 904 to the first member 902 when the boss 912 is inserted into the hole 914. As such, the retaining members 922 each have a size and shape that permits the retaining member 922 to be accommodated in a complementary groove 918, 920 in the boss 912. As an example, the second member 904 can slide along the axis of the boss 912 when the boss 912 is disposed within the hole 914 and the retaining members 922 are disposed within the pair of first grooves 918. Together the retaining members 922 and grooves 918, 920 cooperate, or interact, to form a retaining mechanism. In some implementations, the retaining members 922 can comprise retention springs.

The first member 902 can comprise a plurality of retaining members 922. In some implementations, the first member 902 can comprise two retaining members, collectively at 922, such as in the form of retention springs. The retaining members 922 are each configured to selectably engage the first groove 918 and the second groove 920 of the boss 912, but not at the same time. As will be discussed in more detail below, the retaining members 922 can selectably engage the walls of the first groove 918 to maintain the CMD kerrison-rongeur 900 in a non-operational configuration, or cleaning configuration, during cleaning of the CMD kerrison-rongeur 900. The retaining members 922 can selectably engage the walls of the second groove 920 to maintain the CMD kerrison-rongeur 900 in an operational configuration, or operational tool configuration, during use of the surgical instrument. As an example, the first and second members 902, 904 are maintained in close contact during surgical use.

Transitioning the retaining members 922 from the second groove 920 to the first groove 918 permits the second member 904 to move outward and away from the first member 902 thereby creating a gap (e.g., 226 of FIG. 11B) between the first and second members 902, 904. As an example, the first groove 918 acts as a stop to prevent further relative movement of the first and second members 902, 904 and to expose the gap. The gap between the first and second members 902, 904 is large enough in size so as to avoid forming a cavity that promotes capillary action. In some non-limiting examples, the gap between the first and second members 902, 904 is greater than 0.5 mm but no more than 2.0 mm in size to maintain structural stability. Once the retaining members 922 are received within the first groove 918 or the second groove 920 the retaining members 922 and the walls of the boss 912 interact to removably couple the second member 904 to the first member 902.

The cutting slide 908 of the second member 904 is configured to selectably engage the elongated track member 906 when the first and second members 902, 904 are removably coupled. In some implementations, the track 910 is configured to slidably receive the elongated cutting slide 908 which extends approximately the length of the elongated track member 906. In these implementations, the elongated cutting slide 908 is removably attached to the elongated track member 906. It will be appreciated that any method of fixedly but removably interconnecting the elongated cutting slide 908 of the second member 904 with the elongated track member 906 of the first member 902 in a pivoting, sliding relationship may be utilized in accordance with this disclosure.

In this implementation, the distal end 906*b* of the elongated track member 906 terminates in a first jaw 928 which extends upwardly from the elongated track member 906 in the distal direction at a desired angle. In some implementations, the first jaw 928 extends upwardly from, and approximately perpendicularly to, the elongated track member 906. The distal end 908*b* of the elongated cutting slide 908 terminates in a second jaw 930 which extends downwardly from the elongated cutting slide 908 and is configured to selectively engage with the first jaw 928. The first jaw 928 may extend upwardly for a length approximately equal to the height of the distal end 908*b* of the elongated cutting slide 908. The first jaw 928 may be of any thickness sufficient to withstand the force exerted by the advancement of the elongated cutting slide 908 against the first jaw 928. During surgical use, the first and second jaws 928, 930 of the first and second members 902, 904 cooperate to cut bone and/or tissue of a patient.

The first member 902 and the second member 904 each comprise a handle 916, 932 respectively. For the first member 902, the proximal end 906*a* of the elongated track member 906 terminates in the handle 916 that extends downwardly from the elongated track member 906 in the proximal direction at a desired angle. For the second member 904, the proximal end 908*a* of the elongated cutting slide 908 terminates in the handle 932 that extends downwardly from the elongated cutting slide 908 in the distal direction at a desired angle.

In this implementation, the handles 916, 932 of the respective first and second members 902, 904 may be biased away from each other by biasing members 934, 936. The biasing members 934, 936 each have a top end and a bottom end. The bottom end of first biasing member 934 is integrally formed with the bottom end of the handle 916. The bottom end of the second biasing member 936 is integrally formed with the bottom end of the second handle 932. The top ends of the biasing members 934, 936 include means to interlock the two biasing members 934, 936. When the biasing members 934, 936 are interlocked, they are biased away from each other, thereby biasing the handle 932 distally. Any suitable means may be used to interlock the two biasing members 934, 936. As an example, one biasing member 936 may include a tab 938 or other protrusion at its top end that fits into a notch 940 in the top end of the other biasing member 934.

Although not illustrated, the CMD kerrison-rongeur 900 can be assembled in a similar manner to the CMD kerrison-rongeur 200. For example, the first member 902 is removably coupled to the second member 904 by selectably inserting the boss 912 into the hole 914. In this implementation, the second member 904 is in an extreme squeezed position during insertion. The second member 904 and first member 902 are pushed together until the handle 932 of the second member 904 is disposed in contact with the handle 916 of the first member 902. Before releasing the handle 932 of the second member 904 from the handle 916 of the first member 902, the cutting slide 908 is pushed down onto the track member 906. As the handle 932 of the second member 904 is released tension pushes the distal portion of the cutting slide 908 of the second member 904 forward and urges the CMD kerrison-rongeur 900 towards the operational configuration in which the medical instrument is ready for surgical use. Rotation of the second member 904 relative to the first member 902 causes the boss 912 to undergo corresponding rotation within in the hole 914 such that the second member 904 enters an operational configuration with the retaining members 922 disposed within the second groove 920 of the boss 912.

FIG. 32 shows the CMD kerrison-rongeur 900 in an operational configuration in which an operational medical instrument is formed for surgical use. During surgical use, the handles 916, 932 are squeezed together which causes the cutting slide 908 of the second member 904 to slide forward in the distal direction relative to the track member 910 of the first member 902. In particular, squeezing the handles 916, 932 together causes the jaw 930 of the cutting slide 908 to move towards the jaw 928 of the track member 906 for cutting tissue at the tip.

During surgical use of the CMD kerrison-rongeur 900, the retaining members 922 engage the walls that define the second groove 920 in the boss 912 to keep the first and second members 902, 904 close together. In effect, the boss 912 of the second member 904 is captured by the retaining members 922 positioned within the second groove 920 thereby preventing the second member 904 from disengaging from the first member 902 and, by extension, preventing decoupling. It will be appreciated from this disclosure that the second member 904 and associated elongated cutting slide 908 is free to move "linearly" during surgical use.

FIGS. 33 through 35 show the CMD kerrison-rongeur 900 transition from an operational configuration, such as the operational medical instrument shown in FIG. 32, to a non-operational configuration, or cleaning configuration, that allows for cleaning and sterilizing of the CMD kerrison-rongeur 900, by disengaging and decoupling the first and second members 902, 904 according to the following sequence of steps. First, the handles 916, 932 are moved apart, as represented by arrow D shown in FIG. 33, with the handle 932 of the second member 904 opened to its maximum. Pulling the handles 916, 932 apart allows the elongated cutting slide 908 of the second member 904 to rotate, or spring, upward from the track member 906 of the first member 902, as represented by arrow E shown in FIG. 33. Rotation of the second member 904 relative to the first member 902 causes the boss 912 to undergo corresponding rotation within in the hole 914. This separates the elongated cutting slide 908 from the elongated track member 906 and places the second member 904 in position to be pushed outward in a lateral direction away from the first member

902, as represented by arrow F in FIG. 33 (prior to outward movement). FIG. 34 shows the CMD kerrison-rongeur 900 after the second member 904 has been moved outward in a lateral direction away from the first member 902. Transitioning the CMD kerrison-rongeur 900 from the operational configuration to the non-operational by moving the second member 904 outward in a lateral direction away from the first member 902 causes the retaining members 922 to disengage from the second groove 920 and instead engage the first groove 918 and forms a gap 926 between the first and second members 902, 904. Moving the second member 904 outward in a lateral direction away from the first member 902 can be performed by the person performing the cleaning and sterilization or it can be done by an internal spring (not shown) between the first member 902 and second member 904 around the central axis of the boss 912.

With respect to the gap 926, sliding the second member 904 outward, or laterally, by at least 2.0 mm creates the gap 926, as shown in FIG. 35. The gap 926 is a large cavity that promotes complete rinsing, cleaning, and sterilization of the CMD kerrison-rongeur 900 without any undesirable capillary action. Traditional kerrison-rongeur surgical instruments do not permit such movement between components to form a gap. Additionally, some existing kerrison-rongeur surgical instruments do not allow for the cutting slide to disengage from the track member to form a space (e.g., lumen) therebetween. As a result, existing kerrison-rongeur surgical instruments are difficult to properly clean after use.

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

The invention claimed is:

1. A device for use as a tool, comprising:
a main component formed as a monolithic body, wherein the monolithic body is configured to be selectably transformed by a user between an operational configuration and a non-operational configuration, wherein the transformation from the non-operational configuration to the operational configuration comprises engaging two or more portions of the monolithic body in contact together to form an operational tool that can be operably manipulated by the user, the operational tool comprising a distal tool end, a proximal user engagement end, and one or more hinge points, and wherein the transformation from the operational configuration to the non-operational configuration comprises disengaging the engaged portions from each other;
wherein the monolithic body comprises:
a first member having a proximal end that forms part of the proximal user engagement end of the operational tool and a distal end that forms part of the distal tool end of the operational tool, wherein the first member includes a jaw disposed at the distal end of the first member;
a second member having a proximal end that forms part of the proximal user engagement end of the operational tool and a distal end that forms part of the distal tool end of the operational tool, wherein the second member includes a jaw disposed at the distal end of the second member, wherein the jaws of the first and second members oppose one another and together form a functional tip at the distal tool end of the operational tool that is configured to be operably manipulated by the user by actuating the proximal user engagement end of the operational tool;
a first hinge disposed between the proximal and distal ends of the first and second members, wherein the hinge comprises a first portion on the first member that is configured to mate with a complementary second portion on the second member, wherein the mated first and second portions form a first hinge point and are configured to mechanically interact to render the first hinge pivotable;
a second hinge disposed between the proximal and distal ends of the first and second members, wherein the second hinge comprises a first portion on the first member that is configured to mate with a complementary second portion on the second member, wherein the mated first and second portions form a second hinge point and are configured to mechanically interact to render the second hinge pivotable; and
a biasing member having a first end and a second end, the biasing member extending between the first member and the second member with the first end connected to and integrally formed with the first member and the second end connected to and integrally formed with the second member, the biasing member configured to apply a biasing force to the proximal ends of the respective first and second members.

2. The device of claim 1, wherein the device does not contain tangential surface contacts and does not include cavities of a size that facilitate capillary action when disposed in the non-operational configuration.

3. The device of claim 1, wherein the device is formed from metal or elastomeric polymer.

4. The device of claim 1, wherein the biasing member is a flexible, resilient member that is configured to apply the biasing force to the proximal ends of the respective first and second members when the first and second members are forced towards each other.

5. The device of claim 4, wherein the first member includes a finger loop disposed at the proximal end of the first member, wherein the second member includes a finger loop disposed at the proximal end of the second member, and wherein the finger loops are configured to be actuated to manipulate the functional tip by forcing the finger loops towards each other.

6. The device of claim 1, wherein the jaw of the first member and the jaw of the second member are configured to operatively engage each other to exert a grasping force or biting force when the first and second members are forced towards each other.

7. The device of claim 1, wherein the first end of the biasing member is connected to the first member at or near the proximal end and the second end of the biasing member is connected to the second member at or near the proximal end.

8. The device of claim 1, wherein the first hinge is disposed in a midsection of the operational tool positioned between the proximal user engagement end and the functional tip at the distal tool end, wherein the midsection comprises a first region that includes the first hinge and a second region, wherein the first region is configured to remain pivotable and capable of carrying compression, wherein the second region is disposed proximate to the functional tip and distal to the first region, wherein pivoting at the first hinge of the first region causes the second region of the midsection to open.

9. The device of claim 1, further comprising a ratchet mechanism disposed at the proximal user engagement end of the operational tool, the ratchet mechanism comprising interlocking teeth that engage one another to prevent the first and second members from being moved away from each other.

10. The device of claim 1, wherein the first hinge comprises:

a boss that is configured to mate with a complementary socket adapted to receive the boss to render the first hinge pivotable, wherein the boss is disposed on the first member and the complementary socket is disposed on the second member, or wherein the boss is disposed on the second member and the complementary socket is disposed on the first member; or an engaging protrusion that is configured to mate with a complementary receiving slot adapted to receive the engaging protrusion to render the first hinge pivotable, wherein the engaging protrusion is disposed on the first member and the complementary receiving slot is disposed on the second member, or wherein the engaging protrusion is disposed on the second member and the complementary receiving slot is disposed on the first member.

11. The device of claim 10, wherein the device is configured to transition from the non-operational configuration, which serves as a cleaning configuration, to the operational configuration, which is the operational tool configuration, by:

inserting the boss into the complementary socket to mate the boss with the complementary socket such that, once mated, the first member and the second member are substantially coplanar, and wherein mating the boss with the complementary socket forms the hinge; or inserting the engaging protrusion into the complementary receiving slot to mate the engaging protrusion with the complementary receiving slot such that, once mated, the first member and the second member are substantially coplanar, and wherein mating the engaging protrusion with the complementary receiving slot forms the hinge.

12. The device of claim 11, wherein the device is configured to transition from the operational configuration to the non-operational configuration by:

disengaging the first hinge, wherein disengaging the first hinge comprises:

removing the boss from the complementary socket by linearly moving the boss relative to the socket, along a vertical axis, such that the boss-containing part of the first member and the socket-containing part of the second member are not coplanar; or removing the engaging protrusion from the complementary receiving slot by linearly moving the engaging protrusion relative to the receiving slot, along a vertical axis, such that the engaging protrusion-containing part of the first member and the receiving slot-containing portion of the second member are not coplanar.

13. The device of claim 1, wherein the first member includes a handle disposed at the proximal end of the first member, wherein the second member includes a handle disposed at the proximal end of the second member, and wherein the handles are configured to be actuated to manipulate the functional tip.

14. The device of claim 13, wherein the first hinge is disposed proximate to the jaws and distal to the second hinge, and wherein the second hinge is disposed proximate to the handles.

15. The device of claim 1, wherein:

The first hinge comprises a boss disposed on the first member and a complementary socket disposed on the second member, or the boss disposed on the second member and the complementary socket disposed on the first member; and the second hinge comprises an engaging protrusion disposed on the first member and a complementary slot disposed on the second member, or the engaging protrusion disposed on the second member and the complementary slot disposed on the first member.

16. The device of claim 15, wherein the first member further comprises an intermediate protrusion and a corresponding pocket having an opening configured to receive the intermediate protrusion therein, wherein the intermediate protrusion and corresponding pocket of the first member are disposed between the first hinge and the second hinge; and wherein the second member further comprises an intermediate protrusion and a corresponding pocket having an opening configured to receive the intermediate protrusion therein, wherein the intermediate protrusion and corresponding pocket of the second member are positioned between the first hinge and the second hinge.

17. The device of claim 16, wherein the intermediate protrusion of the second hinge is mated with the corresponding pocket of the first hinge to form a mated pair on either the first or second member, and wherein the mated pairs are configured to transfer force generated by motion of the second hinge to create motion of the first hinge.

18. The device of claim 15, wherein the device is configured to transition from the non-operational configuration, which serves as a cleaning configuration, to the operational configuration, which is the operational tool configuration, by:

inserting the boss into the complementary socket to mate the boss with the complementary socket such that, once mated, the first member and the second member are substantially coplanar, and wherein mating the boss with the complementary socket forms the first hinge; and mating the engaging protrusion with the complementary slot by slidably inserting the engaging protrusion into the complementary slot such that the engaging protrusion is sandwiched between two shelves defining the slot.

19. The device of claim 18, wherein the device is configured to transition from the operational configuration to the non-operational configuration by:

disengaging the second hinge, wherein disengaging the second hinge comprises:

removing the engaging protrusion from the complementary slot by linearly moving the engaging protrusion and slot in opposite directions away from each other while maintaining alignment of the two shelves with two recesses; and disengaging the hinge, wherein disengaging the hinge comprises:

removing the boss from the complementary socket by linearly moving the boss relative to the socket, along a vertical axis, such that the boss-containing part of the first member and the socket-containing part of the second member are not coplanar.

* * * * *